(12) United States Patent
Cazin

(10) Patent No.: US 9,815,765 B2
(45) Date of Patent: *Nov. 14, 2017

(54) RUTHENIUM POLYMERISATION CATALYSTS

(71) Applicant: UNIVERSITY COURT OF THE UNIVERSITY OF ST ANDREWS, St Andrews (GB)

(72) Inventor: Catherine Cazin, St Andrews (GB)

(73) Assignee: University Court of the University of St. Andrews, St. Andrews (GB)

(*) Notice: Subject to any disclaimer, the term of this patent is extended or adjusted under 35 U.S.C. 154(b) by 263 days.

This patent is subject to a terminal disclaimer.

(21) Appl. No.: 14/348,407

(22) PCT Filed: Sep. 28, 2012

(86) PCT No.: PCT/GB2012/000744
§ 371 (c)(1),
(2) Date: Mar. 28, 2014

(87) PCT Pub. No.: WO2013/045876
PCT Pub. Date: Apr. 4, 2013

(65) Prior Publication Data
US 2014/0228563 A1    Aug. 14, 2014

(30) Foreign Application Priority Data
Sep. 28, 2011  (GB) .................................. 1116719.4

(51) Int. Cl.
| | |
|---|---|
| C07F 15/00 | (2006.01) |
| C08G 61/08 | (2006.01) |
| C07C 67/317 | (2006.01) |
| C07C 6/02 | (2006.01) |
| C07C 253/30 | (2006.01) |
| C07C 67/333 | (2006.01) |
| C07C 67/343 | (2006.01) |
| C07F 17/02 | (2006.01) |
| C07D 207/20 | (2006.01) |
| C07D 211/70 | (2006.01) |
| C07D 223/04 | (2006.01) |
| C07D 307/28 | (2006.01) |
| C07F 7/18 | (2006.01) |

(52) U.S. Cl.
CPC .............. *C07C 67/317* (2013.01); *C07C 6/02* (2013.01); *C07C 67/333* (2013.01); *C07C 67/343* (2013.01); *C07C 253/30* (2013.01); *C07D 207/20* (2013.01); *C07D 211/70* (2013.01); *C07D 223/04* (2013.01); *C07D 307/28* (2013.01); *C07F 7/1852* (2013.01); *C07F 15/0046* (2013.01); *C07F 17/02* (2013.01); *C08G 61/08* (2013.01); *C07C 2531/18* (2013.01); *C07C 2531/22* (2013.01); *C07C 2531/30* (2013.01); *C07C 2601/10* (2017.05); *C07C 2601/16* (2017.05); *C07C 2602/22* (2017.05); *C08G 2261/3325* (2013.01); *C08G 2261/418* (2013.01)

(58) Field of Classification Search
CPC .......................... C07F 15/0046; C08G 61/08
See application file for complete search history.

(56) References Cited

U.S. PATENT DOCUMENTS

| | | | |
|---|---|---|---|
| 6,635,768 B1 | 10/2003 | Herrmann et al. | |
| 7,294,717 B2 | 11/2007 | Herrmann et al. | |
| 7,378,528 B2 | 5/2008 | Herrmann et al. | |
| 7,622,590 B1 | 11/2009 | Nolan | |
| 7,652,145 B2 | 1/2010 | Herrmann et al. | |
| 8,153,810 B2 | 4/2012 | Herrmann et al. | |
| 9,233,994 B2 * | 1/2016 | Cazin | C07F 15/0046 |
| 2004/0095792 A1 | 5/2004 | Herrmann et al. | |
| 2005/0013150 A2 | 1/2005 | Herrmann et al. | |
| 2005/0107626 A1 | 5/2005 | Herrmann et al. | |
| 2008/0009598 A1 | 1/2008 | Herrmann et al. | |
| 2008/0207911 A1 | 8/2008 | Herrmann et al. | |
| 2011/0282068 A1 | 11/2011 | Herrmann et al. | |
| 2013/0165649 A1 | 6/2013 | Cazin | |

FOREIGN PATENT DOCUMENTS

| | | | |
|---|---|---|---|
| DE | 19815275 A1 | 10/1999 | |
| WO | WO 2011/117571 A1 | 9/2011 | |

OTHER PUBLICATIONS

Galan et al. "Ligand-Promoted Carbene Insertion into the Aryl Substituent of an N-Heterocyclic Carbene Ligand in Ruthenium-Based Metathesis Catalysts" Journal of the American Chemical Society, 2009, vol. 131, pp. 6822-6832.*

Bantreil et al. "Mixed N-heterocyclic carbene/phosphite ruthenium complexes: towards a new generation of olefin metathesis catalysts" Chemical Communications, 2010, vol. 46, pp. 7115-7117.*

Sutthasupa et al. "Recent advances in ring-opening metathesis polymerization, and application to synthesis of functional materials" Polymer Synthesis and Reactions, 2010, vol. 42, pp. 905-915.*

European Patent Office, International Application No. PCT/GB2012/000744 International Search Report and Written Opinion dated Dec. 14, 2012, pp. 1-13.

Xavier Bantreil et al., "Mixed N-heterocyclic carbene/phosphite ruthenium complexes: towards a new generation of olefin metathesis catalysts," Chem. Commun., 2010,46, Aug. 27, 2010, pp. 7115-7117.

(Continued)

*Primary Examiner* — Joseph Kosack
(74) *Attorney, Agent, or Firm* — Christopher J. Knors; Moore & Van Allen, PLLC

(57) ABSTRACT

Cis and trans ruthenium complexes that can be used as catalysts for ring opening metathesis polymerization (ROMP) are described. The complexes are generally square pyramidal in nature, having two anionic ligands X. Corresponding cationic complexes where one or both of the anionic ligands X are replaced by a non-co-ordinating anionic ligand are also described. Polymers such as polydicyclopentadiene (PDCPD) can be prepared using the catalysts.

13 Claims, 4 Drawing Sheets

(56) References Cited

OTHER PUBLICATIONS

Olivier Songis et al., "An unusual cationic Ru(II) indenylidene complex and its Ru(III) derivative—efficient catalysts for high temperature olefin metathesis reactions," Chem. Commun., 2012,48, Dec. 16, 2011, pp. 1266-1268.

Nguyen, Sonbinh T.. et al.. Ring-Opening Metathesis Polymerization (ROMP) of Norbornene by a Group VIII Carbene Complex in Protic Medica, J. Am. Chem. Soc., 114:3974-3975 (1992).

Schwab, Peter. Eine Reihe definierter Metathesekatalysatoren-Synthese von und Reaktionen mit, Angew. Chem., 107(18):2179-2181 (1995).

Scholl, Matthias, et al., Synthesis and Activity of a New Generation of Ruthenium-Based Olefin Metathesis Catalysts Coordinated with 1,3-Dimesityl-4,5-dihydroimidazol-2-ylidene Ligands, Organic Letters, 1(60):953-956 (1999).

Kingsbury, Jason S., et al, A Recyclable Ru-Based MetathesisCatelyst, J. Am. Chem. Soc., 121:791-799 (1999).

Garber, Steven B., et al, Efficient and Recyclable Monomeric and Dendritic Ru-Based Metathesis Catalysts, J. Am Chem. Soc., 122:8168-8179 (2000).

Grela, Karol, et al., A Highly Efficient Ruthenium Catalyst for Metathesis Reactions, Angew. Chem. Int. Ed., 41(21):4038-4040 (2002).

Wakamatsu, Hideaki, et al., A New Highly Efficient Ruthenium Metathesis Catalyst Angew. Chem., 114(13):2509-2511 (2002).

Zaja, Mirko, et al., Ruthenium olefin metathesis catalysts with modified styrene ethers: influence of steric and electronic effects, Tetrahedron, 59:6545-6558 (2003).

Michrowska, Anna, et al., Nitro-Substituted Hoveyda-Grubbs Ruthenium Carbenes: Enhancement of Catalyst Activity through Electronic Activation, J. Am. Chem. Soc., 126:9318-9325 (2004).

Dragutan, Valerian, et al., Ruthenium Indenylidene Complexes, Metathesis Catalysts with Enhanced Activity, Platinum Metals Rev., 49(1):33-40 (2005).

Clavier, Herve, et al., A pyridine-containing ruthenium-indenylidene complex: Synthesis and activity in ring-closing metathesis, Journal of Organometallic Chemistry, 591:5444-5447 (2006).

Jafarpour, Laleh, et al., Indenylidene-Imidazolylidene Complexes of Ruthenium as Ring-Closing Metathesis Catalysts, Organometallics, 18:5416-5419 (1999).

Clavier, Herve, et al., N-Heterocyclic Carbene and Phosphine Ruthenium Indenylidene Precatalysts: A Comparative Study in Olefin Metathesis, Chem. Eur. J. 13:8029-8036 (2007).

Boeda, Fabien, et al., Ruthenium-Indenylidene Complexes: Scope in Cross-Metathesis Transformations, Adv. Synth. Catal., 350:2959-2966 (2008).

Clavier, Herve, Indenylidene Ruthenium Complex Bearing a Sterically Demanding NHC Ligand: An Efficient Catalysts for Olefin Metathesis at Room Temperature, Organometallics. 28: 2848-2854 (2009).

Furstner, A., et al., Cationic ruthenium allenylidene complexes as a new class of performing catalysts for ring closing metathesis, Chem. Commun., 1315-1316 (1998).

Picquet, Michel, et al., Catalytic synthesis of 3-vinyl-2.5-dihydrofurans from yne-enes promoted by photochemically activated metal-allenylidene LnRu=C=C=CR2 complex: Chem. Commun., 2249-2250 (1998).

Furstner, Alois, et al., Cationic Ruthenium Allenylidene Complexes as Catalysts for Ring Closing Olefin Metathesis, Chem. Eur. J., 6(10):1847-1857 (2000).

Hansen, S Michael. et al., A New Class of Ruthenium Carbene Complexes: Synthesis and Structures of Highly Efficient Catalysts for Olefin Metathesis, Angew. Chem. Int. Ed., 38(9): 1273-1276 (1999).

Hofmann, Peter, et al., Isolation and characterization of a monomeric, solvent coordinated ruthenium(II)carbene cation relevant to olefin metathesis, Journal of Organometallic Chemistry, 606:88-92 (2000).

Volland, Martin August Otfried, et al., Synthesis, Structure and Reactivity of Cationic Ruthenium(II) Carbene Complexes with Bulky Chelating Bisphosphines: Design of Highly Active Ring Opening Metathesis Polymerization (ROMP) Catalysts, Organometallics, 23:800-816 (2004).

Miyaki, Yoshiharu, et al., Co-catatyst dependent cycloisomerization or ring closingmetathesis of alpha, omega-dienes catalyzed by arene ruthenium complex with side-arm alcohol, Journal of Organometallic Chemistry, 616:135-139 (2000).

Wang, Dongren, et al., Cationic Rull Complexes with N-Heterocyclic Carbene Ligans for UV-Induced Ring-Opening Metathesis Polymerization, Angew. Chem. Int. Ed., 47:3267-3270 (2008).

Romero, Patricio, et al., Direct Observation of a 14-Electron Ruthenacyclobutane Relevant to Olefin Metathesis, J. Am., Chem. Soc., 127:5032-5033 (2005).

Romero, Patricio E., et al., Olefin Metathesis Rapidly Initiating Ruthenium Olefin-Metathesis Catalysts, Angew. Chem. Int. Ed., 43:6161-6165 (2004).

Slugovc, Christian, et al., "Second Generation" Ruthenium Carbene Complexes with a cis-Dichloro Arrangement, Organometallics, 23:3622-3626 (2004).

Ung, Thay, et al, Latent Ruthenium Olefin Metathesis Catalysts That Contain an N-Heterocyclic Carbene Ligand, Organometallics, 23:5399-5401 (2004).

Barbasiewicz, Michal. et al, Structure and Activity Peculiarities of Ruthenium Quinoline and Quinoxaline Complexes: Metathesis Catalysts, Organometallics, 25:3599-3604 (2006).

Gstrein, Xaver, et al., Ruthenium Quinoline and Quinoxaline Complexes: Thermally Triggered Initiators for Ring Opening Metathesis Polymerization, Journal of Polymer Science: Part A: Polymer Chemistry, 45:3494-3500 (2007).

Ben-Asuly, Amos, et al. A Thermally Switchable Latent Ruthenium Olefin Metathesis Catalyst, Organometallics, 27:811-813 (2008).

Diesendruck, Charles E., et al., A Latent S-Chelated Ruthenium Benzylidene Initiator for Ring-Opening Metathesis Polymerization, J. Polym. Sci. Part A. Poylm. Chem., 47:4209-4213 (2009).

Diesendruck, Charles E.. et al.. Predicting the Cis-Trans Dichloro Configuration of Group 15-16 Chelated Ruthenium Olefin Metathesis Complexes: A DFT and Experimental Study, Inorg. Chem. 48:10819-10825 (2009).

Ben-Asuly, Amos, et al., Photoactivation of Ruthenium Olefin Metathesis Initiators, Organometallics, 28:4652-4655 (2009).

Tzur, Eyal, et al., Studies on Electronic Effects in O-, N- and S-Chelated Ruthenium Olefin-Metathesis Catalysts, Chem. Eur. J., 16:8726-8737 (2010).

Zirngast, Michaela, et al., Pyridine as trigger for chloride isomerisation in chelated ruthenium bensylidene complexes: implications for olefin metathesis Chem. Commun., 47:2261-2263 (2011).

Love, Jennifer A., et al., Synthesis, Structure. and Activity of Enhanced Initiators for Olefin Metathesis. Journal of the American Chernicai Society, vol. 125 (33), 2003, pp. 10103-10109.

Urbina-Blanco, Cesar A., et al., Olefin Metathesis Featuring Ruthenium Indenylidene Complexes with a Sterically Demanding NHC Ligand. Chemistry—A European Journal, vol. 17 (18), 2011, pp. 5045-5053.

Adekunle, Olubummo. et al., Synthesis and crossover reaction of TEMPO containing block copolymer via ROMP, Beilstein Journal of Organic Chemistry. vol. 6 (59), 2010, pp. 1-11.

Kovacic, Sebastijan, et al., Inherently reactive polyHIPE material from dicyclopentadiene. Chemical Communications, vol. 46 (40), 2010, pp. 7504-7506.

Schmid, Thibault E., et al., Phosphites as ligands in ruthenium-benzylidene catalysts for olefin metathesis, Chemical Communiciations, vol. 47 (25). 2011, pp. 7060-7062.

Leitgeb, Anita, et al., "Two commercially available initiators for the retarded ring-opening metathesis polymerization of dicyclopentadiene" Manatsh Kim, vol. 145, 2014, pp. 1513-1517.

Urbina-Blanco, Céesar A., et al., "The Activation Mechanism of Ru-Indenylidene Complexes in Olefin Metathesis" Journal of the American Chemical Society, vol. 135, pp. 7073-7079.

Sanford, Melanie S., et al., "Mechanism and Activity of Ruthenium Olefin Metathesis Catalysts" Journal of the American Chemical Society, vol. 123, No. 27, 2001, pp. 6543-6545.

(56) References Cited

OTHER PUBLICATIONS

Pump, Eva, et al., "Variation of the Sterical Properties of the N-Heterocyclic Carbene Coligand in Thermally Triggerable Ruthenium-Based Olefin Metathesis Precatalysts/Initiators" Organometallics, vol. 34, Nov. 9, 2015, pp. 5383-5392.

Grubbs, Robert H., et al., "Mechanism and Activity of Ruthenium Olefin Metathesis Catalysts" J. Am. Chem. Soc., vol. 123, 2001, pp. 6543-6554.

* cited by examiner

RUTHENIUM POLYMERISATION CATALYSTS

CROSS-REFERENCE TO RELATED APPLICATIONS

This application is filed under the provisions of 35 U.S.C. §371 and claims the benefit of International Patent Application No. PCT/GB2012/000744, filed on Sep. 28, 2012, which claims the benefit of Patent Application No. 1116719.4, filed in Great Britain on Sep. 28, 2011; all of which are hereby incorporated by reference in their entirety.

The work leading to this invention has received funding from the European Research Council under the European Community's Seventh Framework Programme (FP7-NMP-2007-SMALL-1) "EUMET"/ERC grant agreement no. NMP2-SL-2009-211468.

FIELD OF THE INVENTION

The present invention relates to the provision of ruthenium complexes, their manufacture and uses for example in catalysis, in particular in olefin metathesis reactions, including in Ring Opening Metathesis Polymerisation (ROMP).

BACKGROUND TO THE INVENTION

Olefin metathesis is considered as one of the most useful tools in organic chemistry. Since Grubbs reported the first generation ruthenium-catalyst (ref 1), numerous studies have been aimed at developing long life and more active catalysts and precatalysts. A breakthrough was the replacement of a phosphine ligand by a N-heterocyclic carbene (NHC), increasing the reactivity and stability of the corresponding complex (ref 2). See G-II in Scheme 1 below where $PCy_3$ is tricyclohexylphosphine. Additional modifications afforded so-called boomerang-type catalysts, the most well-known being Hoveyda's catalyst (Hov-II in scheme 1 below) (refs 3,4). In such catalysts the benzylidene bears a donor atom that binds to Ru and decoordinates during catalysis to recoordinate after. More recently, replacing the benzylidene group of Grubbs original catalysts by an indenylidene moiety resulted in highly stable catalysts (for example M2 in scheme 1 where $PCy_3$ is tricyclohexylphosphine) (ref 5).

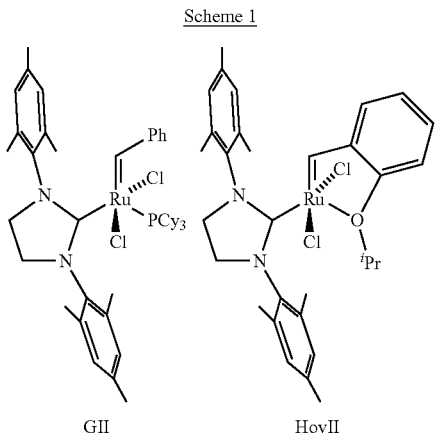

Scheme 1

GII          HovII

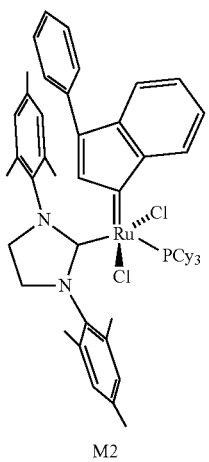

M2

This family of catalysts has proved its efficiency in various metathesis transformations, and studies on the variation of the NHC group have already been reported (ref 6).

Other examples of Ruthenium catalysts for use in metathesis transformations are described in U.S. Pat. No. 7,622,590.

Some cationic ruthenium complexes are known for use as catalysts and are shown in Scheme 1a below. For example Fürstner and Dixneuf (ref 7) have described 18-electron cationic allenylidene Ru complexes such as (a) below that were found to be catalyst precursors for ring closing metathesis (RCM). Hofmann (ref 8) describes dinuclear 16-electron cationic ruthenium complexes with chelating bisphosphane ligands (b), displaying activity in ring opening metathesis polymerization (ROMP). Kurosawa et al (ref 9) describe 18-electron cationic ruthenium complexes (c) made by chloride abstraction using silver salts. A latent cationic ruthenium NHC-based pre-catalyst (d) with excellent ROMP properties activated by UV irradiation has also been reported (ref 10). Complexes (e) are described by Romero et al (ref 11).

Scheme 1a

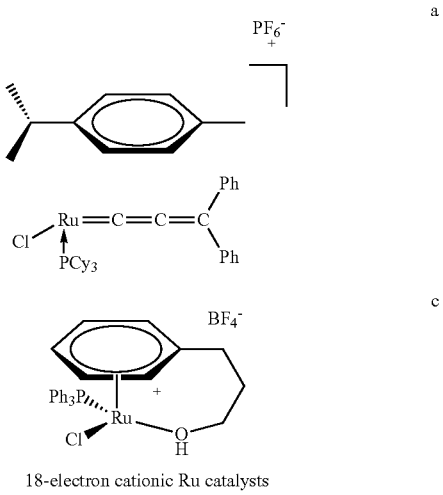

18-electron cationic Ru catalysts

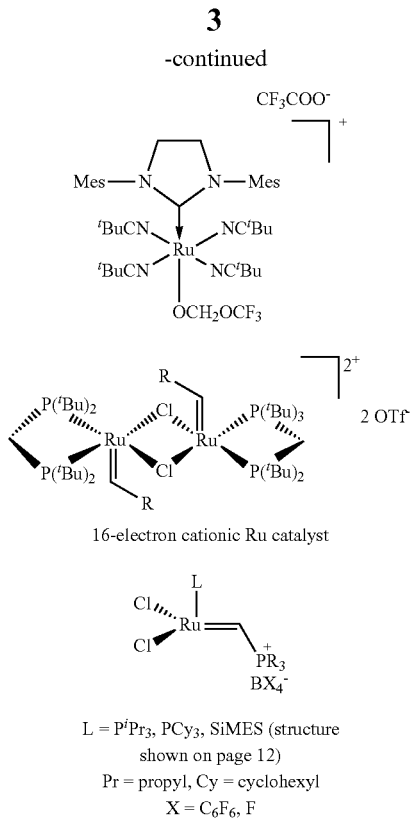

16-electron cationic Ru catalyst

L = P$^i$Pr$_3$, PCy$_3$, SiMES (structure shown on page 12)
Pr = propyl, Cy = cyclohexyl
X = C$_6$F$_6$, F In view of the importance of olefin metathesis chemistry there remains the need to provide yet further metathesis catalysts. Some further catalysts are described in an earlier application (PCT/GB2011/000404) by the same inventor as the present application, the entire contents of which are incorporated by reference herein.

DESCRIPTION OF THE INVENTION

According to a first aspect the present invention provides a cis ruthenium complex according to general formula I:

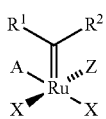
I wherein for each occurrence the groups X are the same or different and are anionic ligands or are fused to form a bidentate ligand;
the groups R$^1$ and R$^2$ are the same or different and are selected from the group consisting of hydrogen, C1-C20 alkyl, C2-C20 alkenyl, C2-C20 alkynyl, C2-C20 alkoxycarbonyl, aryl, C1-C20 carboxylate, C1-C20 alkoxy, C2-C20 alkenyloxy, C2-C20 alkynyloxy, aryloxy, C1-C20 alkylthio, C1-C20 alkylsulfonyl, and C1-C20 alkylsulfinyl,
each R$^1$ and R$^2$ optionally being substituted (for example with C1-C5 alkyl, halogen, C1-C10 alkoxy, or with a phenyl group that may itself be substituted, for example with halogen, C1-C5 alkyl or C1-C5 alkoxy); or
the groups R$^1$ and R$^2$ are fused together to form a ring (for example C4-C10, or even C5-C6) that may be substituted or unsubstituted, saturated or unsaturated and may be fused to a further ring (for example C4-C10 or even C5-C6); and
the group Z is selected from the group consisting of:

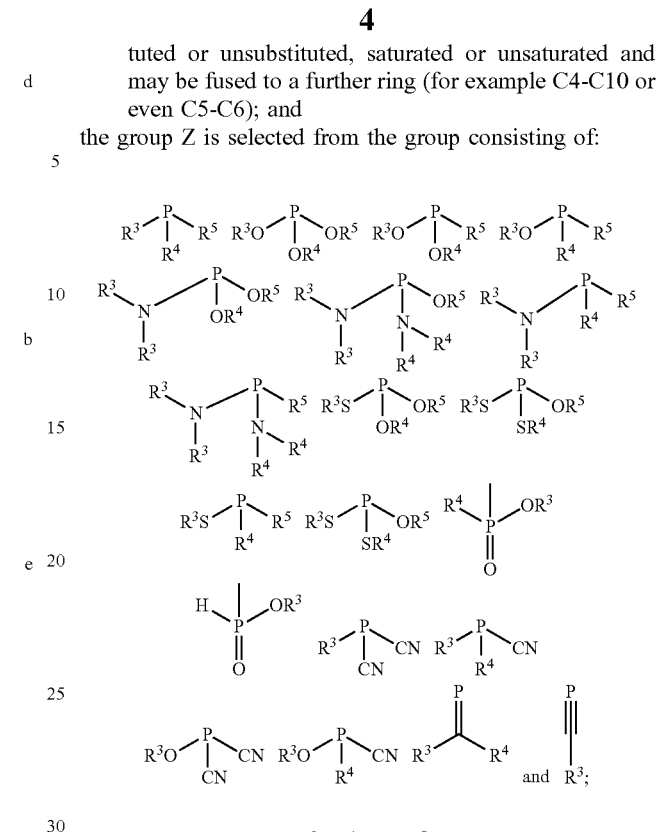

wherein the groups R$^3$, R$^4$ and R$^5$ are each independently for each occurrence selected from the group consisting of substituted or unsubstituted primary, secondary or tertiary alkyl, that may be cyclic and may be unsaturated (for example C1-C10 or even C1-C4); substituted or unsubstituted aryl or heteroaryl; optionally two or more of the groups R$^3$, R$^4$ and R$^5$ are fused to form a ring; and
the group A is selected from the group consisting of a nucleophilic carbene, and a phosphorus ligand independently selected from the list of groups as defined for group Z; and with the proviso that when A is a nucleophilic carbene, Z is not

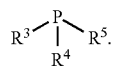

Groups R$^3$,R$^4$,R$^5$ may be substituted, for example once, twice, or three times, e.g. once, i.e. formally replacing one or more hydrogen atoms of the alkyl, aryl or heteroaryl group. Examples of such substituents when are halo (e.g. fluoro, chloro, bromo and iodo), SF$_5$, CF$_3$, aryl, aryl hydroxy, nitro, amino, alkoxy, alkylthio, carboxy, cyano, thio, formyl, ester, acyl, thioacyl, amido, sulfonamido, carbamate and the like. Where the substituent is amino it may be NH$_2$, NHR or NR$_2$, where the substituents R on the nitrogen may be alkyl, aryl or heteroaryl (for example substituted or unsubstituted C1-C20 or even C1-C10).

Where the groups R$^3$,R$^4$,R$^5$ are cycloalkyl they may be for example cyclohexyl or cyclopentyl. The cyclohexyl or cyclopentyl groups if present may be saturated or unsaturated and may be substituted as described above. By aryl is meant herein a radical formed formally by abstraction of a hydrogen atom from an aromatic compound. As known to those skilled in the art, heteroaryl moieties are a subset of aryl moieties that comprise one or more heteroatoms, typically O, N or S, in place of one or more carbon atoms and any hydrogen atoms attached thereto. Exemplary $R^3, R^4, R^5$ aryl substituents, for example, include phenyl or naphthyl that may be substituted. Exemplary $R^3, R^4, R^5$ heteroaryl substituents, for example, include pyridinyl, furanyl, pyrrolyl and pyrimidinyl. Further examples of heteroaromatic rings include pyridazinyl (in which 2 nitrogen atoms are adjacent in an aromatic 6-membered ring); pyrazinyl (in which 2 nitrogens are 1,4-disposed in a 6-membered aromatic ring); pyrimidinyl (in which 2 nitrogen atoms are 1,3-disposed in a 6-membered aromatic ring); or 1,3,5-triazinyl (in which 3 nitrogen atoms are 1,3,5-disposed in a 6-membered aromatic ring).

The complexes of formula I are of a generally square pyramidal structure and are cis in the sense that the groups A and Z are adjacent to each other, whilst the two groups X are adjacent to each other.

In the complexes of the invention the groups Z (and A when A is a phosphorus ligand) bond to Ru by the phosphorus atom. An example of a cis complex where A is a nucleophilic carbene and Z is a phosphine (tricylohexylphosphine—$PCy_3$) is known (ref 12) as shown below.

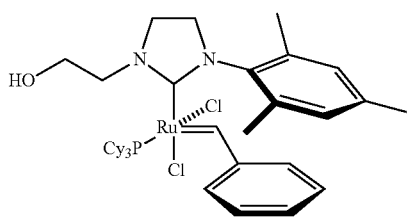

A small number of related cis Ru complexes have previously been described (refs 12, 13), but all have a chelating ligand present in the structure. For example the group Z is replaced with a moiety that coordinates to Ru via a heteroatom (e.g. O,N,S) that is covalently joined to the alkylidene (carbene) moiety double bonded to the Ru to form an alkylidene chelating ligand. Alternatively a bidentate diphosphine ligand may be used. Examples of prior art cis dichloride structures are shown below.

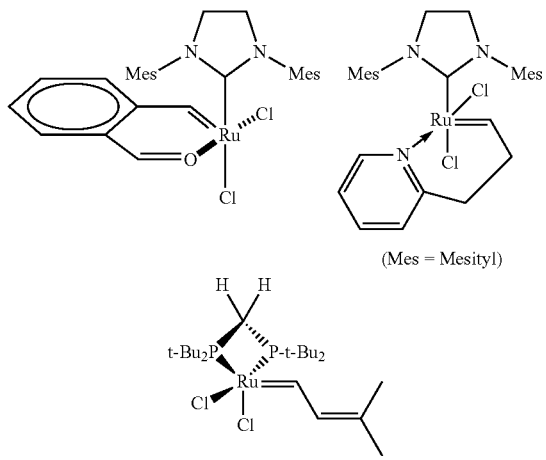

In contrast the cis complexes of the present invention have monodentate groups Z. The complexes of the invention are useful catalysts as described below. By providing complexes without bidentate A-Z ligands (for example alkylidene) or bidentate diphosphine ligands, greater opportunity is afforded to tune the behaviour of the catalyst as the groups A and Z can each be changed independently.

The trans complexes of formula II shown below where A, Z, $R^1$ and $R^2$ have the same meaning as in formula I constitute a second aspect of the present invention, with the provisos that both groups Z and A are not phosphine;

and where A is a nucleophilic carbene, Z is not a phosphine:

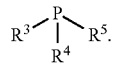

A number of trans complexes such as complex M1 below where both A and Z are phosphine are already known, as are trans complexes GII and M2 where Z is a phosphine and A is an NHC.

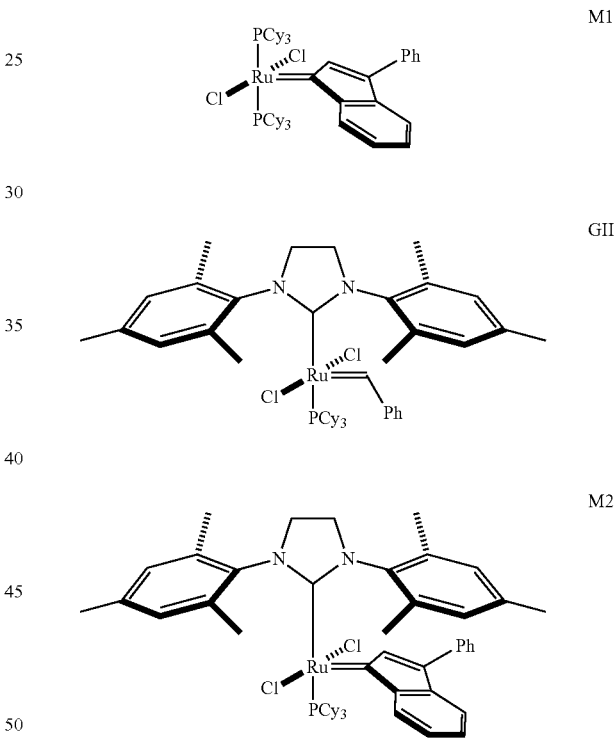

The trans complexes have groups X opposite each other and groups A and Z opposite each other.

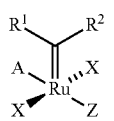

It will be appreciated that further isomerism is possible for both the cis and trans forms (formulas I and II). For example enantiomeric pairs may be produced as a consequence of the square pyramidal geometry. For example the enantiomeric pair of cis isomers I and Ia below.

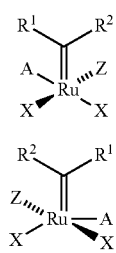

I

Ia

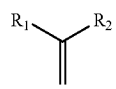

includes an ester). The structure is given below.

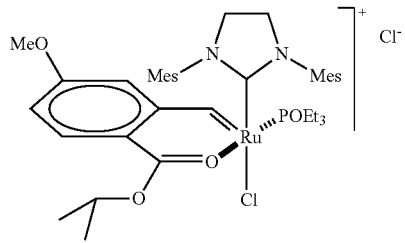

(Mes = mesityl)

In this description of the invention it is to be understood that structures drawn define the cis or trans positioning of the groups A, Z and X but otherwise a given structure includes all possible isomers. Thus cis structure I is to be understood to include structure Ia. Further isomerism is possible, for example where $R^1$ and $R^2$ are different or are fused to form a ring that is not symmetrical then geometric isomerism about the carbon to ruthenium double bond may occur.

In the cis and trans complexes of the invention the anionic ligands X may be, for example, independently selected from the group consisting of halogen (I, Br, Cl, F), benzoate, $C_1$-$C_5$ carboxylates (for example $CF_3CO_2$, $CH_3CO_2$, $CFH_2CO_2$, pivalate), $C_1$-$C_5$ alkoxy (for example, MeO, EtO, $(CH_3)_3CO$, $(CF_3)_3CO$, $(CF_3)_2(CH_3)CO$, $(CF_3)(CH_3)_2CO$) phenoxy, $C_1$-$C_5$ alkyl thio groups, tosylate, mesylate, brosylate, trifluoromethane sulfonate, phenylacetate and pseudo-halogens (for example cyanide, thiocyanate, isothiocyanate, selenocyanate).

In particular embodiments, both anions X are chloride. Alternatively ligands X can be fused to each other, forming a bidendate anionic ligand. For instance, acac (acetylacetonate).

As an alternative one or both of the groups X in formulas I or II above may be replaced by a non-co-ordinating anionic ligand to provide cationic ruthenium complexes of formula VIII, IX or X:

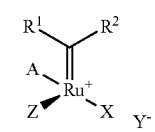

VIII

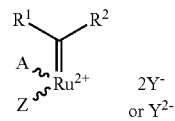

IX

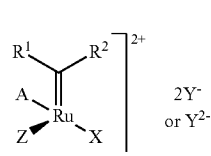

X wherein groups $R^1$, $R^2$, A and Z have the same meaning as described above in respect of Formulas I and II but without the provisos attached to the definitions. Complexes of formula X have an Ru (III) metal centre to balance the charge provided by the remaining anionic co-ordinating ligand X and the non-co-ordinating anionic ligand(s) $Y^-$ or $Y^{2-}$.

A cationic complex making use of phosphite and NHC ligands has been described (ref 14) but only when making use of a bidentate ligand (the group As described above with respect to complexes of formula I, the use of monodentate Z, A and

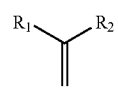

ligands affords the opportunity to tune each of the substituents on the complex for its intended uses e.g. as a catalyst.

$Y^-$ or $Y^{2-}$ are non-coordinating ionic ligands that may be the same or different for each occurrence. The non-coordinating anionic ligands $Y^-$ may be selected from the group consisting of $SbF_6^-$, $BF_4^-$, $PF_6^-$, $ClO_4^-$, $[B[3,5-(CF_3)_2C_6H_3]_4]^-$ and $BPh_4^-$. The non-coordinating anionic ligands $Y^{2-}$ may be selected from the group consisting of Oxide ($O^{2-}$), Hydrogen phosphate ($HPO_4^{2-}$), Sulfide ($S^{2-}$), Chromate ($CrO_4^{2-}$), Sulfate ($SO_4^{2-}$), Dichromate ($Cr_2O_7^{2-}$), Thiosulfate ($S_2O_3^{2-}$), Carbonate ($CO_3^{2-}$), Sulfite ($SO_3^{2-}$), Oxalate ($C_2O_4^{2-}$) and Peroxide ($O_2^{2-}$).

In some instances complexes of formulas VIII, IX or X may have vacant positions about the Ru metal centre occupied by a neutral ligand such as a solvent molecule. For example pyridine or acetonitrile as shown hereafter with reference to a specific complex. Thus, for example, complexes of the forms shown below, where W is a neutral ligand can be formed.

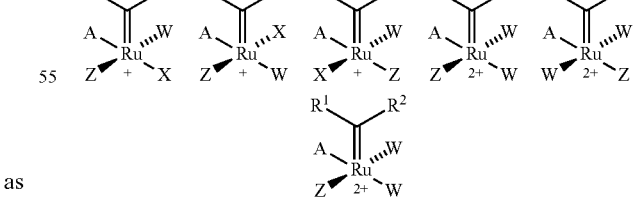

As for formulas I and II (discussed above) isomerism is possible with some of these complexes and the formulas VIII and IX (including those with neutral ligands—W) as shown should be understood to include all possible isomers. For example the complex VIII may exist in two optical isomeric forms VIII and VIIIa below and the structure VIII should be understood to include either or both these possibilities as well as geometric isomers such as VIIIb.

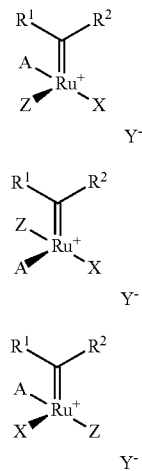

For any of formulas I, II, VIII, IX and X the groups $R^1$ and $R^2$ may be H and aryl (for example phenyl or substituted phenyl)

Where the groups $R^1$ and $R^2$ are fused to form a ring, the ring may have another ring fused to it, for example to form an indenylidene moiety. The indenylidene moiety may be substituted, for example a 3-phenylindenylidene moiety such as employed in M2 of Scheme 1 (above).

Advantageously in the complexes described herein the group Z is phosphite i.e.

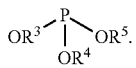

Where the group Z is a phosphite group:

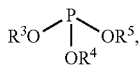

examples include $P(OMe)_3$ $P(OEt)_3$, $P(O^iPr)_3$ and $P(OPh)_3$. As described above the groups $R^3, R^4, R^5$ may be substituted. For use as catalysts, variation of the substituents $R^3, R^4, R^5$ of groups Z, in particular phosphite groups Z, can provide useful adjustment of the properties of the complexes described herein. For example where Z is $P(OPh)_3$ the properties of the complex as a catalyst may be adjusted by substituents on the phenyl ring.

Examples of combinations of A and Z for the complexes described herein, where Z is phosphite, include nucleophilic carbene (in particular N-heterocyclic carbene)/phosphite, phosphine/phosphite and phosphite/phosphite.

Examples of group A as a phosphine include $PCy_3$ and $PPh_3$—where Cy is cyclohexyl and Ph is phenyl. Examples of group A as a phosphite include $P(OMe)_3$ $P(OEt)_3$, $P(O^iPr)_3$ and $P(OPh)_3$.

Where the group A is an nucleophilic carbene, the carbene may have a four, five, six or seven membered ring containing the carbene carbon. Typically a five-membered ring. The nucleophilic carbene may be an N-heterocyclic carbene (NHC).

The NHC employed may be saturated or unsaturated and may contain one or more nitrogen atoms and optionally may contain other heteroatoms (such as O and S) in the ring.

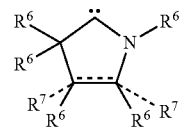

For example the ligand may have the form above wherein the groups $R^6$ may be the same or different, the groups $R^7$ where present may be the same or different and the dashed line in the ring represents optional unsaturation. One or more of the carbon atoms in the ring (apart from the carbene carbon) may be substituted with O or S. Each $R^6$ and $R^7$ may be, independently for each occurrence, selected from: H, a primary or secondary alkyl group (for example C1-C10 or even C1-C4) that may be substituted or unsubstituted, substituted or unsubstituted phenyl, substituted or unsubstituted naphthyl, or substituted or unsubstituted anthracenyl, or a functional group selected from the group consisting of halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy.

Advantageously NHC ligands bearing two nitrogen atoms in the ring, each adjacent the carbene carbon may be employed. The NHC carbene ligands of this type may have the form:

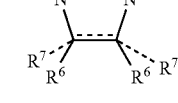

wherein each of the groups $R^6$, $R^7$ and $R^8$ may be the same or different for each occurence and the dashed line in the ring represents optional unsaturation, wherein $R^7$ is absent. Each $R^6$, $R^7$ and $R^8$ may be, independently for each occurrence, selected from: H, a primary or secondary alkyl group (for example C1-C10 or even C1-C4) that may be substituted or unsubstituted, substituted or unsubstituted phenyl, substituted or unsubstituted naphthyl, or substituted or unsubstituted anthracenyl, or a functional group selected from the group consisting of halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy.

Advantageously the groups $R^8$ may be substituted or unsubstituted aromatic rings that may be heterocyclic aromatic rings. Substituents $R^6$, $R^7$ and $R^8$ in the structures above may include alkyl and unsaturated alkyl groups, aryl groups that may be substituted and may contain heteroatoms.

Suitable examples of NHC carbene ligands include those according to formulas III to VI below:

For example these NHC carbenes:

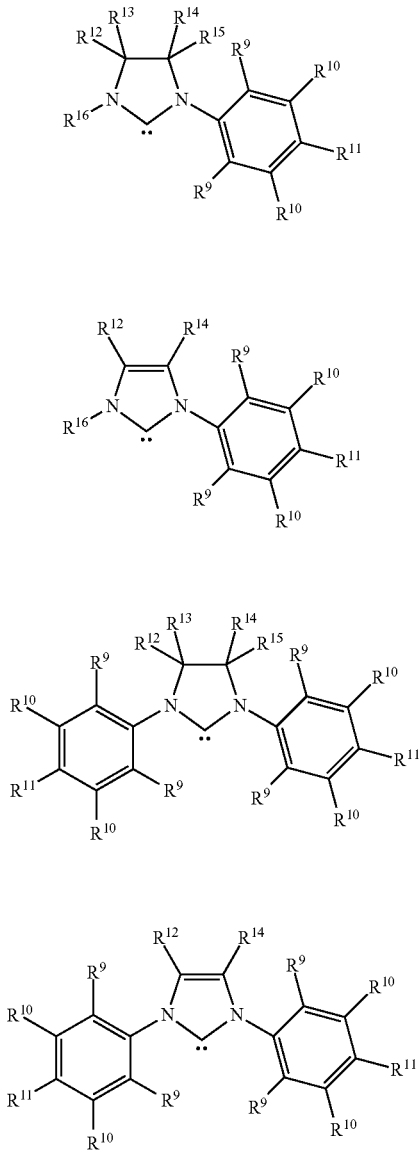

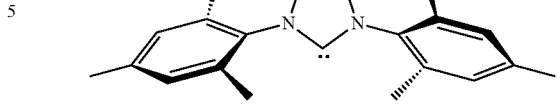

IMes

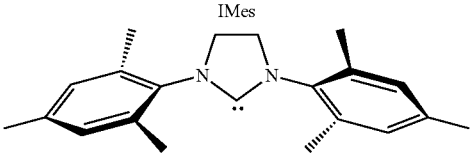

SIMes

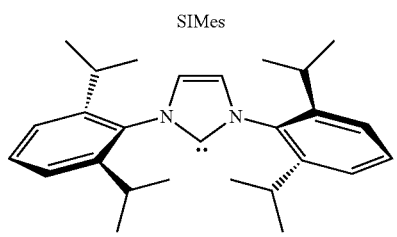

IPr

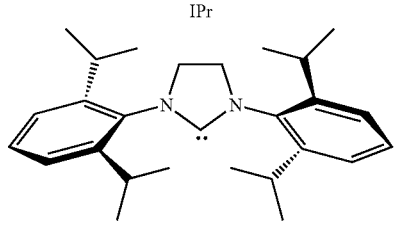

SIPr are suitable examples of the NHC carbene family for the formation of the ruthenium complexes, the alkyl substituted aromatic rings providing additional stabilisation to the carbene lone pair of electrons.

The desired ruthenium phosphite complexes may be made by substitution of a suitable leaving group from a precursor ruthenium complex. For example from 1 in Scheme 2 below, (wherein SIMes is the NHC:

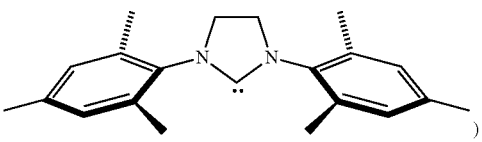

by a route analogous to that used for the production of ruthenium phosphine complexes.

For example, complex 1 was reacted with different phosphites (1 equiv) in dichloromethane and stirred for 1 h at room temperature. This procedure can produce a mixture of two complexes, each presenting $^{31}$P NMR shifts corresponding to chelated phosphites—between 110 and 135 ppm (free phosphites have signals around 128-145 ppm). The two complexes have been shown to be cis and trans forms as shown for the example using P(O$^i$Pr)$_3$ (complexes 2) of Scheme 2 and discussed hereafter with reference to specific examples.

wherein each group $R^9$, $R^{19}$ and $R^{11}$, is independently for each occurrence selected from: H, a primary or secondary alkyl group (for example C1-C10 or even C1-C4) that may be substituted or unsubstituted, substituted or unsubstituted phenyl, substituted or unsubstituted naphtyl, or substituted or unsubstituted anthracenyl, or a functional group selected from the group consisting of halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy; $R^{12}$, $R^{13}$, $R^{14}$ and $R^{15}$ are each independently for each occurence H, a substituted or unsubstituted alkyl group (for example C1-C10 or even C1-C4), substituted or unsubstituted aryl, or in formulas (IV) and (VI) together with the carbons carrying them form a substituted or unsubstituted, fused 4-8 membered carbocylic ring or a substituted or unsubstituted, fused aromatic ring, preferably a fused phenyl ring; and $R^{16}$ is alkyl (for example C1-C10 or even C1-C4) or a cycloalkyl (for example C3-C8).

Scheme 2

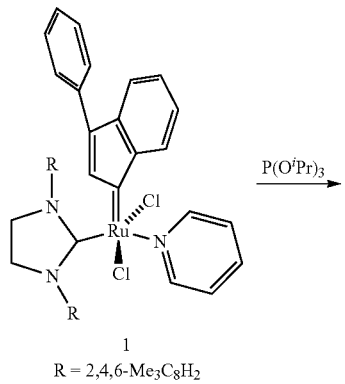

1
R = 2,4,6-Me$_3$C$_8$H$_2$

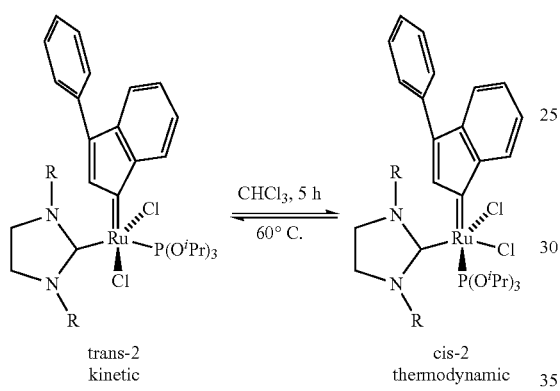

trans-2
kinetic cis-2
thermodynamic

The trans form (phosphite opposite to NHC) is kinetically favoured compared to the cis form (phosphite adjacent the NHC) which is the thermodynamic product. Thus the trans form is produced in higher yield than the thermodynamically more stable cis at lower temperatures. The trans form is readily converted to the cis by heat as indicated in Scheme 2.

X-ray studies of cis-2 have shown that it was actually produced as a mixture of two enantiomers as indicated below.

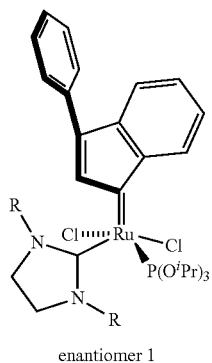

enantiomer 1

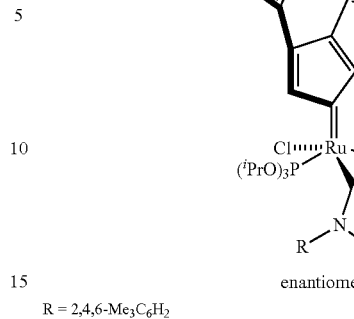

enantiomer 2
R = 2,4,6-Me$_3$C$_6$H$_2$

According to a third aspect the present invention provides a method of preparing a ruthenium complex according to general formula I:

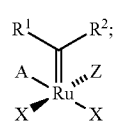

I wherein the groups A,X,Z, R$^1$ and R$^2$ have the same meaning as before, the method comprising:

providing a complex according to general formula VII:

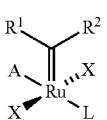

VII where L is a leaving group and A,X, R$^1$ and R$^2$ have the same meaning as before; and reacting the complex of formula VII with a compound comprising or consisting of a group Z wherein Z has the same meaning as before.

The leaving group L may be for example a substituted or unsubstituted pyridine, phosphine, phosphite, phosphinite, phosphonite, phosphoramidate, thiophene, tetrahydrofuran, N heterocyclic carbene, acetonitrile or benzonitrile. In some examples the leaving group L may be linked covalently to the group

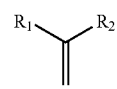

to form a bidentate ligand. An example is given in the synthesis of a cis complex 65 described hereafter.

The method may further comprise heating to convert trans complex (formula II) to cis complex (formula I). Thus the method can make complexes of formula II as well as those of formula I. Generally the method to prepare the complexes of the invention from the complex according to general formula VII from is carried out in a suitable solvent, typically a chlorinated solvent such as dichloromethane. Thermal conversion of a trans complex to a cis complex may be accomplished by heating in a suitable solvent such as, for example chloroform, toluene or nitromethane.

Complexes of formulas VIII and IX may be made, for example by starting with a complex of formula I or formula II and displacing one of the coordinating ligands X. For example where X is halogen reaction with a silver salt of the anion Y⁻ (e.g. AgSbF$_6$) can produce the products of formula VIII, or X. The method is illustrated in Scheme 3 below, where anionic ligand X is chloride in this example. Surprisingly reaction of an example complex of formula I where X is chloride with two equivalents of AgSbF$_6$ did not produce a complex of formula IX, but rather a complex of formula X wherein one chloride was retained on the ruthenium, which was oxidised to the Ru III species shown. The method of preparing these cationic Ru complexes is another aspect of the present invention.

Scheme 3

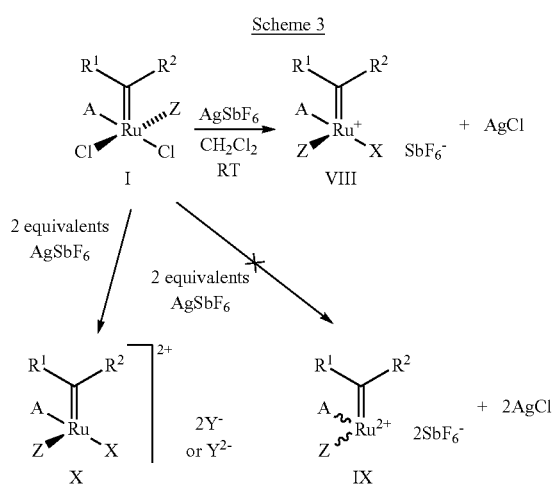

The complexes described herein can be used as catalysts.

Thus according to a fourth aspect the present invention provides use of a complex according to general formula Is

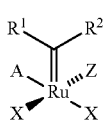

as a catalyst, wherein the groups A,X,Z, R¹ and R² have the same meaning as before.

Complexes where Z is phosphite and A is an NHC have been shown to perform well in a range of catalytic duties as discussed hereafter and with reference to specific examples.

Thus according to a fifth aspect the present invention provides use of a complex according to general formula II:

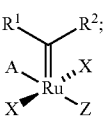

as a catalyst, wherein the groups A,X,Z, R¹ and R² have the same meaning as before.

Thus according to a yet further aspect the present invention provides use of a complex according to general formula VIII, IX or X:

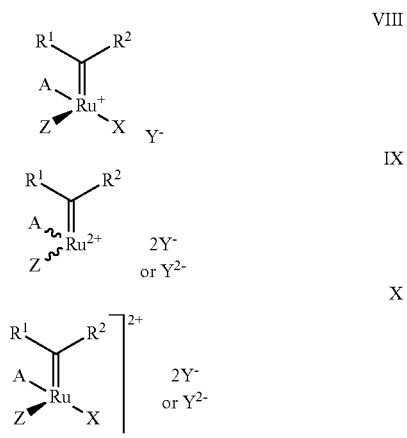

or a complex according to these formulas, wherein at least one vacant position about the metal centre is occupied by a neutral ligand, as a catalyst.

Notably the trans complexes of formula II can show good catalytic activity at room temperature but the cis form (formula I) generally requires higher temperatures, suggesting that the cis form is a latent catalyst. Thus the trans form may be preferred in low temperature situations but as shown below at even moderate temperatures high conversion rates can be obtained when using the cis form. Furthermore the cis forms of the complexes are robust at elevated temperature, showing reduced tendency to loss of activity with time.

The complexes may be used to catalyse a reaction selected from the group consisting of, for example, ring closing metathesis (RCM), enyne ring closing metathesis (enyne RCM), cross metathesis (CM) and ring opening polymerisation metathesis (ROMP). Results obtained are discussed hereafter and with reference to specific examples.

Where the complexes described herein are employed for ROMP catalysis those that behave as latent catalysts may be used advantageously. Their latent catalyst behaviour, i.e. performing as catalysts when the temperature is elevated, allows particularly convenient processing when, for example, polydicyclopentadiene products are prepared from dicyclopentadiene.

ROMP products are generally prepared by Reaction Injection Moulding (RIM) where the monomer, catalyst and any other components are injected into a mould under high pressure. On reaction a solid, moulded, product is prepared.

In order to prevent uncontrolled or premature polymerisation previous catalyst systems for ROMP, in particular for polydicyclopentadiene (PDCPD) production have generally been provided as a two part system, with each part being dissolved or dispersed in a separate lot of monomer. The two monomer lots are then carefully mixed on injection into the mould where reaction occurs as the catalyst system is completed.

With catalysts of the present invention showing latent behaviour, the monomer and any other components can be loaded into a mould (under pressure if required), with the catalyst already dissolved or dispersed within the monomer etc if desired. A small quantity of a suitable solvent, for example a chlorinated solvent such as dichloromethane may be employed to provide a solution of the catalyst.

Reaction can then be initiated in a controlled fashion by heating to an appropriate temperature as described hereafter with reference to specific embodiments. Typically temperatures in the range 30° C. to 120° C. or even 40° C. to 100° C. may be utilised. These relatively low reaction temperatures are convenient as monomers such as dicyclopentadiene have low boiling points Alternatively, where a catalyst is selected that initiates reaction at lower temperatures, a procedure including mixing the catalyst into the monomer mixture as it is introduced into a mould may be used.

Furthermore remarkably low catalyst loadings, of the order of 1 to 100 ppm in relation to monomer or even 5 to 60 ppm may be successfully employed in ROMP procedures making use of complexes of the invention as catalysts.

In general ROMP using catalysts of the invention may be performed using as monomer any of the ring systems already known to undergo such processes.

Suitable monomers for use in ROMP with the catalysts can include dicyclopentadiene, norbornene, norbornadiene, cyclooctadiene and derivatives, such as substituted derivatives of these monomers, thereof. Mixtures of monomers may also be employed and/or other components such as reinforcing fibres and fillers as known to those skilled in the art.

Complexes of the invention wherein an NHC carbene is provided as group A and a phosphite is provided as group Z have been shown to be suitable for use in ROMP polymerisation. The NHC carbene may be selected from those described herein above, for example it may be one of:

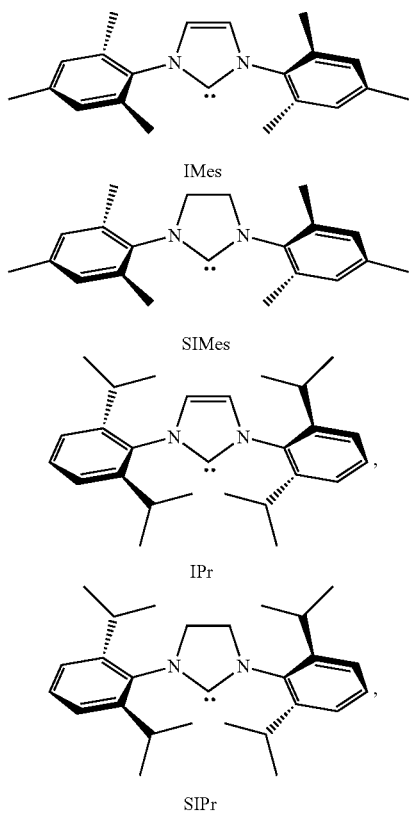

Complexes where the NHC is SIPr and A is a phosphite have been shown to perform well in ROMP procedures, in particular where A is tri-isopropyl phosphite as described hereafter and with reference to a particular example of a trans complex showing latent catalyst behaviour.

BRIEF DESCRIPTION OF THE DRAWINGS

Further features and advantages of the present invention will appear from the following detailed description of some embodiments illustrated with reference to the accompanying drawings in which.

DESCRIPTION OF SOME PREFERRED EMBODIMENTS AND EXPERIMENTAL RESULTS

Preparation of Complexes of Formulas I and II Including an NHC

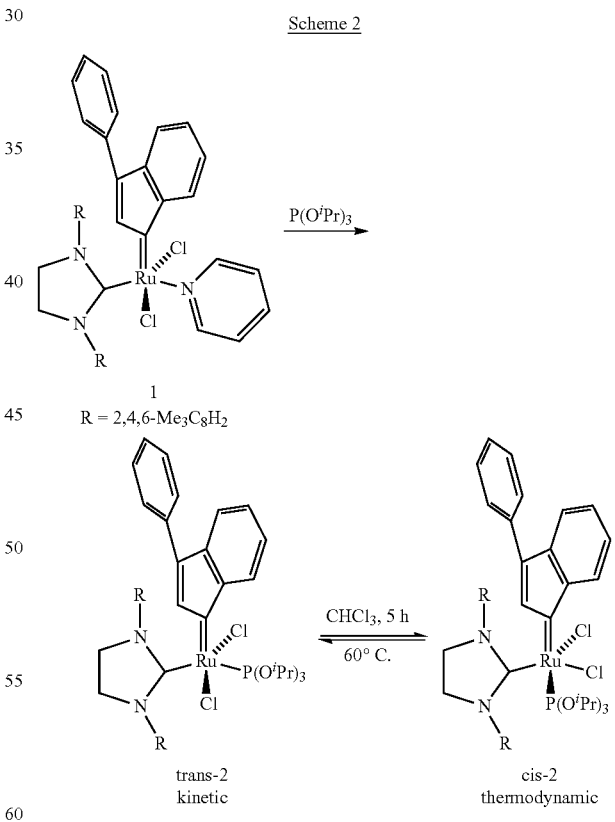

A general procedure is to react complex 1 of scheme 2 above with different groups Z, phosphites in these examples. Phosphites (1-4 equiv) in dichloromethane were reacted with 1 and stirred for 3-15 h at 60° C. This procedure led, whatever the phosphite employed was, to a mixture of two new complexes, presenting $^{31}$P NMR shifts corresponding to coordinated phosphites—between 110 and 135 ppm whereas free phosphites are around 128-145 ppm.

Where the phosphite ligand was P(OiPr)$_3$, as shown in Scheme 2 the conditions described above allow a 90% pure complex ($^{31}$P NMR in CDCl$_3$, major: δ=113 ppm, minor: δ=123 ppm), to be isolated as a red powder. NMR experiments in d$_8$-toluene showed that, after 1 h at 80° C., the complex presenting a chemical shift at 113 ppm was highly converted into the one at 123 ppm. The latter complex was thus isolated and characterized.

Figure 1A:
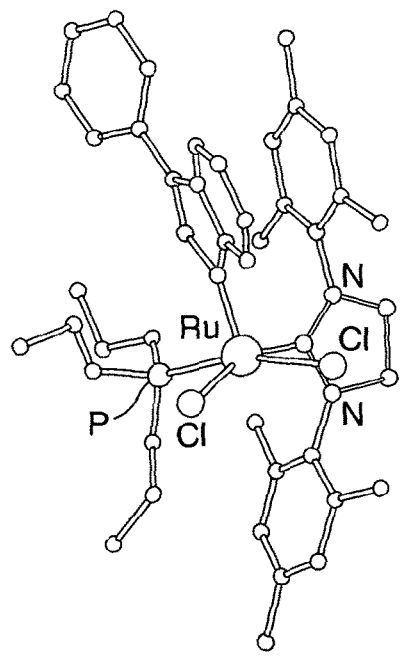
FIGS. 1a to 1d show X-ray structures of complexes of the invention.
Figure 1B:
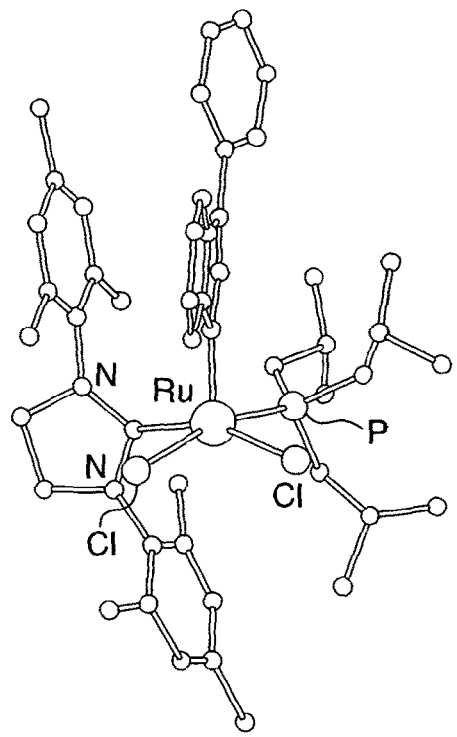
Figure 1C:
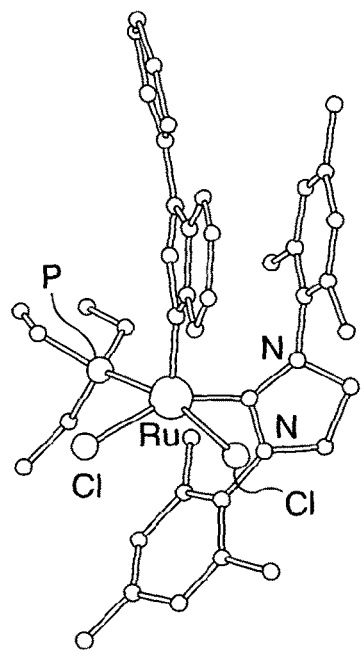
Figure 1D:
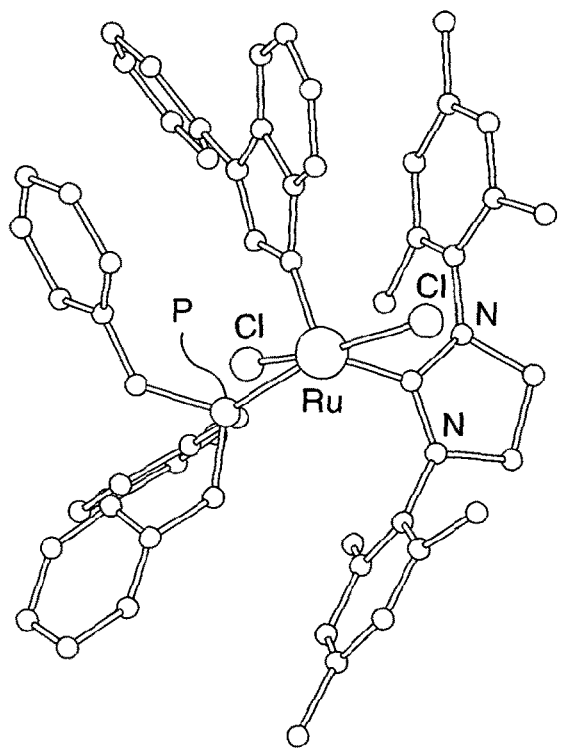

$^1$H NMR of the two complexes showed interesting differences on the phosphite alkoxy groups. Indeed, nicely resolved doublets corresponding to the six equivalent terminal methyl groups of the isopropyl groups in the first complex were found inequivalent in the latter complex, indicating that the free rotation of the phosphite was no longer possible. In addition, $^{13}$C NMR experiments were conducted to observe, in both complexes, the J coupling between the NHC carbenic carbon and the phosphite phosphorus. While the firstly generated complex ($^{31}$P, δ=113 ppm) displayed a carbenic carbon at 208.9 ppm with a classical coupling constant $J_{C\text{-}P}$=124 Hz, the second complex ($^{31}$P, δ=127 ppm) displayed an unusual small coupling of 13 Hz. These observations led to the conclusion that complex trans-2, featuring a trans configuration between the NHC and the phosphite, was obtained kinetically while cis-2 was thermodynamically favored (scheme 2). Complex cis-2 could also be isolated on a larger scale in a good yield of 86% by heating trans-2 in chloroform at 60° C. for 5 h. Interestingly, aspect and solubility were completely different for trans-2 and cis-2. Indeed, while trans-2 was isolated as a red powder that is soluble in polar and apolar solvents, cis-2 is a black solid completely insoluble in pentane, indicating a dependence of physical properties to spatial arrangement. The structure of cis-2 has been confirmed by X-ray crystallography, following growth of a suitable crystal from CH$_2$Cl$_2$/n-dodecane. (See FIG. 1b). The X-ray data also show that the complex cis-2 is present as a pair of enantiomers as discussed above.

In order to obtain cis-complexes directly, with different phosphite ligands, 1 and a selected phosphite were stirred at 40° C. in dichloromethane for the appropriate time (Table 1, below). Following the reaction by $^1$H and $^{31}$P NMR furnished showed different conversion rates. As a general trend, reactivity was dependent on the cone angle of the phosphite. Indeed, the reaction was found to be slower with bulky phosphites such as P(OiPr)$_3$ and P(OPh)$_3$, (15 h), while smaller phosphites such as P(OMe)$_3$ required only 3 h at 40° C. For P(OPh)$_3$, 4 equiv of P(OPh)$_3$ were necessary to obtain relatively fast conversion to the desired complex. With these conditions, complexes cis-2-5 (Table 1) were isolated in yields up to 88%, For cis-3 the lower yield was due to purification difficulties. X ray structures of cis-4, cis-2, cis-3 and cis-5 are shown in FIGS. 1a to 1d respectively.

TABLE 1

Synthesis of cis-Ru-Phosohite complexes[a]

| Entry | P(OR)$_3$ (equiv) | θ (°)[b] | [Ru] complex | Time | Yield (%) |
|---|---|---|---|---|---|
| 1 | P(OMe)$_3$ (1) | 107 | cis-3 | 3 h | 57 |
| 2 | P(OEt)$_3$ (1) | 109 | cis-4 | 5 h | 88 |

TABLE 1-continued

Synthesis of cis-Ru-Phosohite complexes[a]

| Entry | P(OR)$_3$ (equiv) | θ (°)[b] | [Ru] complex | Time | Yield (%) |
|---|---|---|---|---|---|
| 3 | P(OiPr)$_3$ (1) | 128 | cis-2 | 15 h | 84 |
| 4 | P(OPh)$_3$ (4) | 130 | cis-5 | 15 h | 76 |

[a]Reaction conditions: 1 (1 equiv), phosphite, CH$_2$Cl$_2$, 40° C.
[b]Tolman cone angle.

Figure 2:
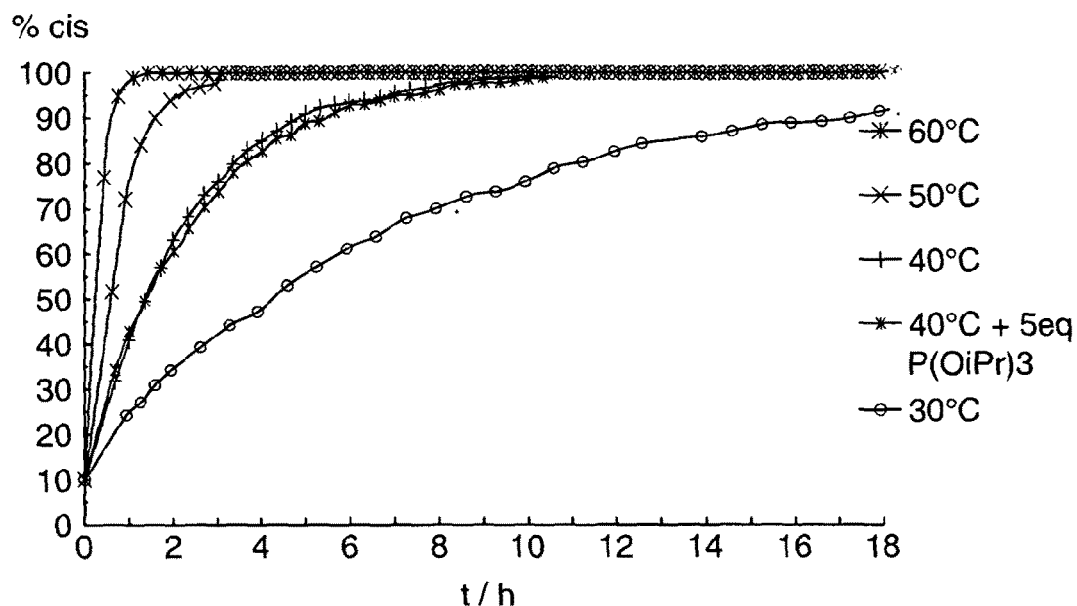
FIG. 2 shows graphically trans to cis isomerisation of complexes of the invention.
Figure 3:
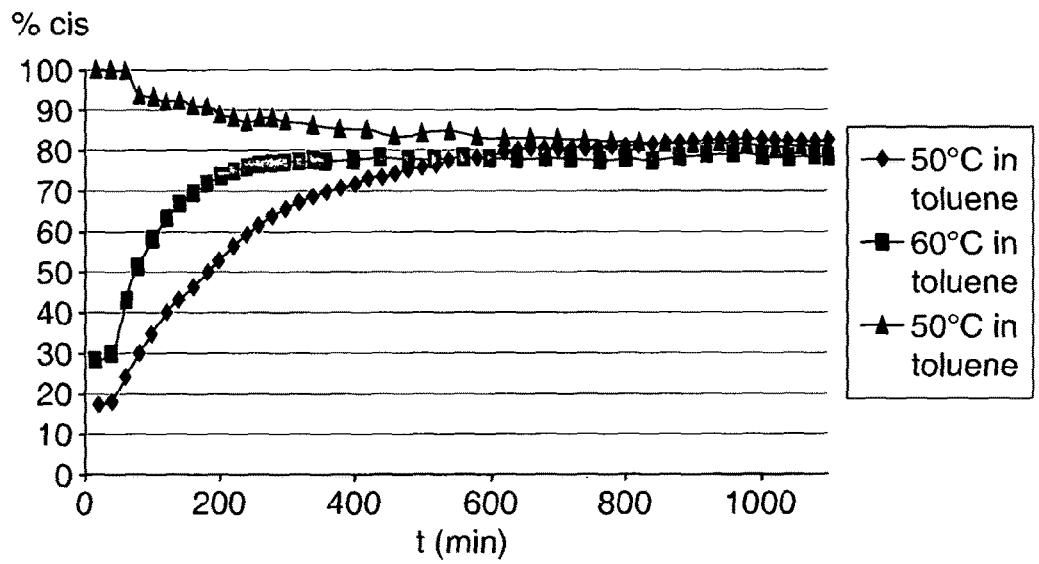
FIG. 3 shows graphically trans to cis isomerisation of complexes of the invention.

NMR studies in CD$_3$NO$_2$ and toluene-d$_8$ (FIGS. 2 and 3 respectively) show the thermal conversion from trans to cis of a sample that contained 90% trans: 10% cis complex 2.

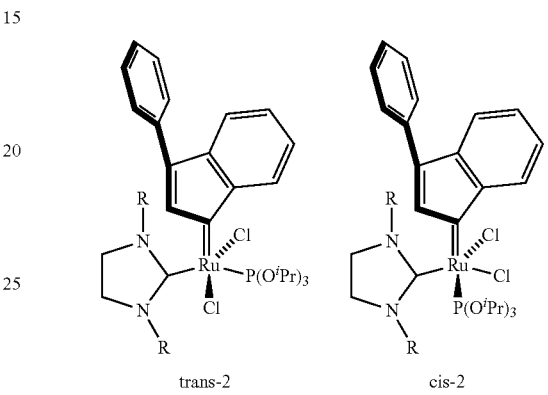

trans-2          cis-2

All the experiments shown were followed by NMR starting from the trans-2 complex complex (pure at 90%, with 10% of cis isomer), except in toluene one experiment at 50° C. started from the pure cis-2. As we can see, polar solvents (nitromethane) favored the formation of the cis isomer whereas apolar solvent (toluene) reached an equilibrium cis/trans 80:20. It seems that a temperature of 30° C. is too low to allow fast conversion. Starting from the cis isomer and heating in toluene led also to a mixture cis/trans 80:20. The first set of curves allowed the calculation of ΔH=22.6 kcal/mol and ΔS=-4.2 cal/mol.

A further example of a synthesis producing an NHC containing cis complex is shown below.

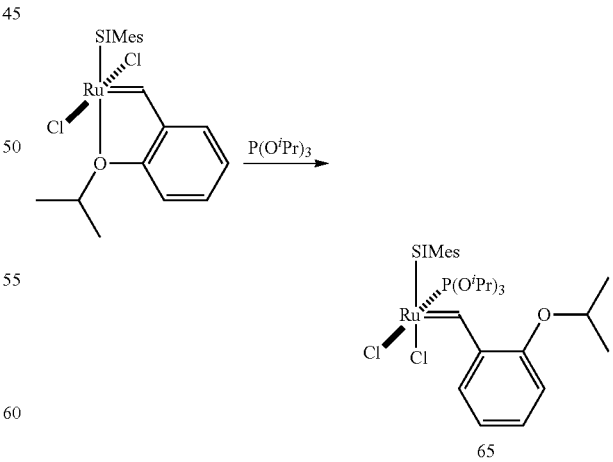

HII (200 mg) and P(O$^i$Pr)$_3$ (5 eq) were stirred in for 72 h. The crude 65 was recrystallised from DCM/pentane.

$^1$H (400 MHz, 298K): 16.05 (d, 1H, J=35.3 Hz, C=CH), 10.24 (d, 1H, J=9.7 Hz, Ph-H), 6.87-6.83 (m, 2H, Ph-H), 6.78 (s, 1H, Ph-H), 6.61 (s, 1H, Ph-H), 6.19-6.16 (m, 2H, Ph-H), 4.67 (brs, 2H, PO—CH—CH$_3$), 4.09-4.06 (m, 1H, Ph-O—CH—CH$_3$), 4.04 (brs, 1H, PO—CH—CH$_3$), 3.43-3.40 (m, 1H), 3.16-3.02 (m, 3H), 2.89 (s, 3H, Mes-CH$_3$), 2.58 (s, 3H, CH$_3$), 2.46 (s, 3H, CH$_3$), 2.42 (s, 3H, CH$_3$), 2.18 (s, 3H, CH$_3$), 1.92 (s, 3H, CH$_3$), 1.48-0.80 (m, 24H, PO—CH—CH$_3$).

$^{31}$P{$^1$H} (121.49 MHz, 298K): 128.7 (s)

Catalytic Activity of Complexes of Formulas I and II

Catalytic activity of complexes was evaluated in ring closing metathesis (RCM), enyne ring closing metathesis (enyne RCM) and cross metathesis (CM). The difference of behavior between trans-2 and cis-2 was studied. The main difference appeared when reactions were run at room temperature. Indeed, whereas trans-2 was able to achieve RCM of diallyltosylamine 6, albeit with lower activities compared to previously reported indenylidene ruthenium complexes, cis-2 was found to be totally inactive at room temperature, even after 24 hours of reaction (Table 2, below, entry 1). Nevertheless, with the same substrate, thermal activation at 80° C. in toluene allowed fast conversion in the presence of cis-2. The same trend was observed in RCM with diallyllic malonate 8, in enyne RCM with 10 and CM with alkene 12 (Table 2, entries 2-4), trans-2 being active at rt while cis-2 needed thermal activation. Such behavior corresponds to a latent catalyst. In order to evaluate the thermal stimulation needed to activate cis-2, RCM of 6 was monitored at different temperatures (25, 40, 60 and 80° C.), the temperature being changed every 30 minutes. No conversion was observed at room temperature and 40° C., 4% conversion at 60° C., and full conversion at 80° C. As a consequence, the comparative study of complexes cis-2 to 5 was conducted at 80° C.

In Table 2 below results for known complexes M2 (scheme 1) and 1 (pyridine containing complex of scheme 2) are also shown for comparison purposes.

TABLE 2

Behaviour of trans-2 vs cis-2.[a]

| Entry | Substrate | Product | catalyst [mol %] | T [° C.] | t [h] | conv. [%][b] |
|---|---|---|---|---|---|---|
| 1 | 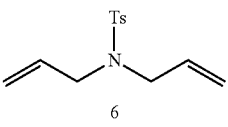 [SMILES: C=CCN(CC=C)S(=O)(=O)c1ccc(C)cc1] 6 | 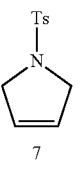 [SMILES: Cc1ccc(S(=O)(=O)N2CC=CC2)cc1] 7 | trans-2 (1) | rt | 5 | 18 |
|   |   |   |   |   | 24 | 88 |
|   |   |   | cis-2 (1) | rt | 24 | 0 |
|   |   |   |   | 40 | 0.5 | 0 |
|   |   |   |   | 60 | 0.5 | 4 |
|   |   |   |   | 80 | 0.5 | >99 |
| 2 | 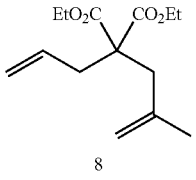 [SMILES: C=CCC(CC(=C)C)(C(=O)OCC)C(=O)OCC] 8 | 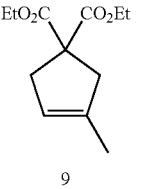 9 | 1 (1) | rt | 5 | 38 |
|   |   |   | M2 (1) | rt | 5 | 82 |
|   |   |   | trans-2 (1) | rt | 5 | 80 |
|   |   |   | cis-2 (1) | rt | 24 | 0 |
|   |   |   |   | 80 | 0.5 | >99 |
| 3 | 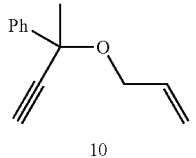 10 | 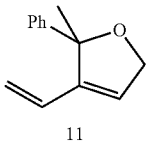 11 | 1 (1) | rt | 24 | 12 |
|   |   |   | M2 (1) | rt | 24 | 63 |
|   |   |   | trans-2 (1) | rt | 24 | 52 |
|   |   |   | cis-2 (1) | rt | 24 | 0 |
|   |   |   |   | 80 | 0.5 | >99 |
| 4 | 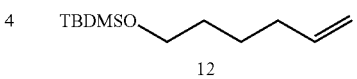 12 | 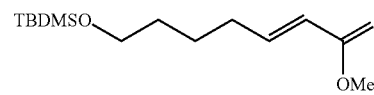 13 | trans-2 (2) | rt | 8 | 65 |
|   |   |   | cis-2 (2) | rt | 8 | 0 |
|   |   |   | cis-2 (2) | 80 | 0.5 | 90 |
|   |   |   |   |   | 1.75 | 97 |

[a]Reaction conditions: substrate (0.25 mmol), catalyst (1-2 mol %), solvent (0.1M, CH$_2$Cl$_2$ and toluene for reactions respectively at room temperature and 80° C.).

[b]Average of 2 runs; conversions were determined by $^1$H NMR.

Complexes were studied as catalysts in RCM of diene, enyne and in CM (Table 3 below). Known complexes 1 (pyridine containing complex of scheme 2, known as M31), M1 and M2 (scheme 1) were also included in some experiments for comparison purposes.

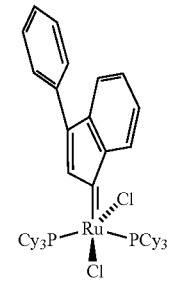

M1

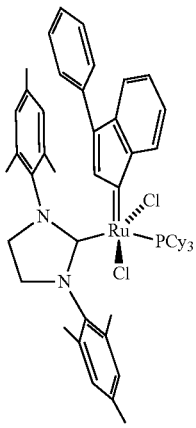

M2

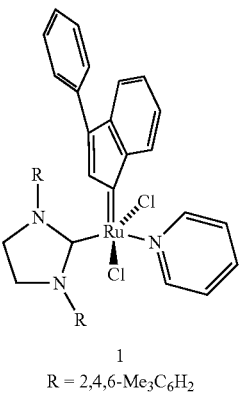

M31

1
R = 2,4,6-Me$_3$C$_6$H$_2$

These complexes are available from Umicore N.V.; Broekstraat 31 rue du Marais B-1000 Brussels, Belgium.

A general trend was found between reactivity and the phosphite substituent for the new complexes. Triisopropyl phosphite and triphenyl phosphite-containing complexes cis-2 and 5 were found to have comparable efficiency, the former one being slightly more active. Indeed, after 30 minutes, RCM of 8 was achieved with cis-2 while traces of 8 could still be detected with cis-5. Even clearer evidences were provided with reactions of 10 and 12, cis-2 being faster than cis-5. Finally, cis-3 and 4, featuring respectively trimethyl and triethylphosphite were similar but far less reactive than cis-2 and 5. Very slow reactivity was observed in the reactions tested, even if a longer reaction time could probably reach full conversion. In order to explore the applicability of such catalysts in metathesis transformations, we chose to run reactions with catalyst cis-2 and at elevated temperature.

TABLE 3

Behaviour of cis-2-5.[a]

| Entry | Substrate | Product | catalyst [mol %] | T [° C.] | t [h] | conv. [%][b] |
|---|---|---|---|---|---|---|
| 1 | 8 | 9 | cis-2 (1) | 80 | 0.5 | >99 |
| | | | cis-3 (1) | 80 | 0.5 | 78 |
| | | | | | 1 | >99 |
| | | | cis-4 (1) | 80 | 0.5 | 35 |
| | | | | | 1 | 73 |
| | | | cis-5 (1) | 80 | 0.5 | 98 |
| | | | | | 1 | >99 |
| | | | 1 (0.5) | 80 | 0.5 | >99 |
| | | | M1 (0.5) | 80 | 0.5 | >99 |
| | | | M2 (0.5) | 80 | 0.5 | >99 |
| | | | trans-2 (0.5) | 80 | 0.5 | >99 |
| 2 | 10 | 11 | cis-2 (0.5) | 80 | 0.5 | 72 |
| | | | | | 1.75 | >99 |
| | | | cis-3 (0.5) | 80 | 1.75 | 5 |
| | | | cis-4 (0.5) | 80 | 1.75 | 10 |
| | | | cis-5 (0.5) | 80 | 1.75 | 91 |

TABLE 3-continued

Behaviour of cis-2-5.[a]

| Entry | Substrate | Product | catalyst [mol %] | T [° C.] | t [h] | conv. [%][b] |
|---|---|---|---|---|---|---|
| 3 | TBDMSO<br>12 | TBDMSO<br>OMe<br>13 | cis-2 (2) | 80 | 0.5<br>1.75 | 90<br>97 |
| | | | cis-3 (2) | 80 | 0.5<br>1.75 | 6<br>38 |
| | | | cis-4 (2) | 80 | 0.5<br>1.75 | 13<br>67 |
| | | | cis-5 (2) | 80 | 0.5<br>1.75 | 60<br>94 |

[a]Reaction conditions: substrate (0.25 mmol), catalyst (0.5 to 2 mol %), toluene (0.1M), 80° C.
[b]Conversions were determined by $^1$H NMR.

A study of the RCM of several substrates has also been carried out. Reactions were run in toluene at 80° C. in the presence of 1 to 5 mol % of cis-2, the higher catalyst loading being only necessary for the formation 17 featuring a tetra-substituted double bond (Table 4 below, entry 3). The RCM of unhindered malonate derivatives was achieved in short reaction times (less than 1 hour) and in good yields. Indeed, di- and tri-substituted cyclopentenes 15 and 9 were obtained in quantitative yields (entries 1 & 2). Nevertheless, highly constrained substrate 16 could not be cyclized with full conversion, even after 24 h at 80° C., and was isolated in 70% yield (entry 3). Finally, b- and 7-membered rings 19 and 21 were obtained in respectively 96 and 87% yield, and no increase in reaction time compared to 5-membered ring 15 (entries 4 & 5). Of note, a dilution to 0.05M was necessary to obtain 21 without observing parallel formation of polymers. We next attempted the RCM of cyano analogues 24 and 26 (entries 6 & 7). Non-hindered cyclopentene 23 was isolated in good yield (88%), indicating that the presence of potentially chelating cyano groups was not detrimental to catalysis. Nevertheless, cis-2 was unable to promote the formation of 25, the starting material remaining unreacted. Tosylamine-based olefins were next investigated. The cyclization of these compounds was found very efficient regardless of hindrance and ring size. Indeed, 5-, 6- and 7-membered compounds 7, 27 and 29 were isolated in excellent yields (entries 8-10), albeit a slight increase in reaction time was needed for larger rings. Catalyst loading of only 2 mol % was necessary to achieve the cyclizations of 30 and 32 to obtain tetrasubstituted 5- and 6-membered rings 31 and 33 in good yields (entries 11 & 12), even so 5 hours of reaction were needed for dihydropyrrole 31. Amide and ether-based substrates were also efficiently cyclized, with yields spanning from 80% to 99% (entries 13-17). Increasing the ring size to 6 or 7 members was not detrimental, as products 39, 41 and 43 were obtained excellent yields in less than 1 hour (entries 15-17). From this study, catalyst cis-2 seemed to be highly tolerant to functionalities and able to effect RCM easily.

Figure 4:
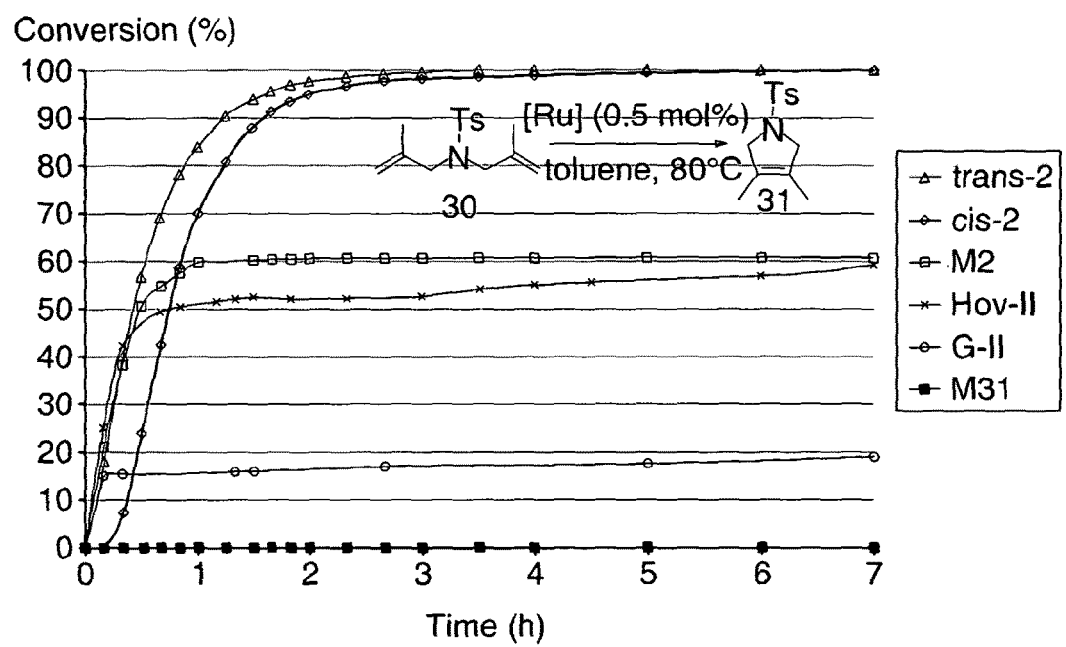
FIG. 4 shows graphically results of ring closure metathesis experiments using various catalysts.

This utility of the complexes of the invention is illustrated further in FIG. 4 which shows RCM of compound 30 (table 4 entry 11) in toluene at 80° C. carried out with a range of Ru complexes. Trans or cis-2 both rapidly produce a high conversion whereas prior art complexes Hov-II, M2 (structures shown in Scheme 1) and M31 (which is the pyridine complex 1 in scheme 2) did not produce any better than about 60% conversion (complex M2) under these conditions.

TABLE 4

Ring closing metathesis behavior of cis-2[a]

| Entry | Substrate | Product | t [h] | conv. [%][b] |
|---|---|---|---|---|
| 1 | EtO$_2$C  CO$_2$Et<br>14 | EtO$_2$C  CO$_2$Et<br>15 | 0.5 | >99 (99) |
| 2 | EtO$_2$C  CO$_2$Et<br>8 | EtO$_2$C  CO$_2$Et<br>9 | 0.5 | >99 (99) |

TABLE 4-continued
Ring closing metathesis behavior of cis-$2^a$
| Entry | Substrate | Product | t [h] | conv. [%][b] |
|---|---|---|---|---|
| $3^c$ | 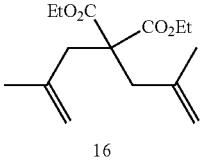 [SMILES: C=C(C)CC(CC(=C)C)(C(=O)OCC)C(=O)OCC] 16 | 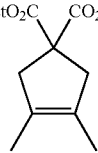 17 | 24 | 82 (70) |
| 4 | 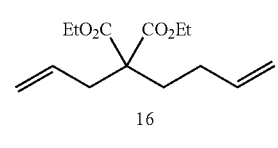 [SMILES: C=CCCC(CC=C)(C(=O)OCC)C(=O)OCC] 16 | 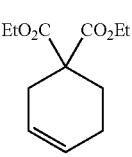 19 | 0.5 | >99 (96) |
| $5^d$ | 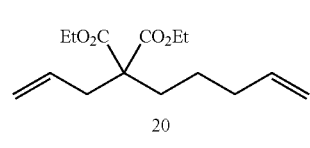 [SMILES: C=CCCCC(CC=C)(C(=O)OCC)C(=O)OCC] 20 | 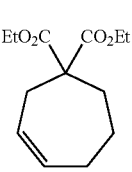 21 | 1 | >99 (87) |
| 6 | 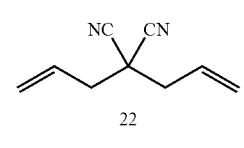 22 |  23 | 0.5 | >99 (88) |
| $7^c$ | 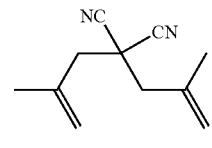 24 |  25 | 24 | 0 |
| 8 | 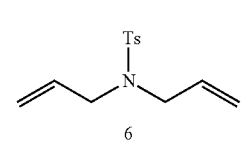 [SMILES: C=CCN(CC=C)S(=O)(=O)c1ccc(C)cc1] 6 | 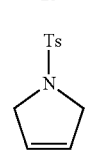 7 | 0.5 | >99 (97) |
| 9 | 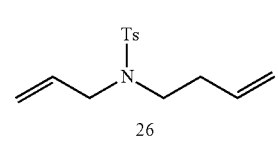 26 | 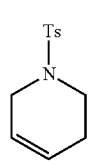 27 | 1.25 | >99 (99) |
| 10 | 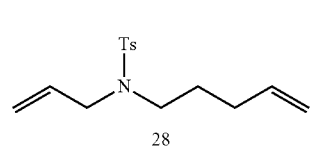 [SMILES: C=CCCCN(CC=C)S(=O)(=O)c1ccc(C)cc1] 28 | 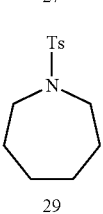 29 | 1 | >99 (88) |

TABLE 4-continued

Ring closing metathesis behavior of cis-2[a]

| Entry | Substrate | Product | t [h] | conv. [%][b] |
|---|---|---|---|---|
| 11[e] | 30 | 31 | 5 | >99 (95) |
| 12[e] | 32 | 33 | 1.5 | >99 (99) |
| 13 | 34 | 35 | 0.5 | >99 (99) |
| 14 | 36 | 37 | 0.75 | >99 (80) |
| 15 | 36 | 39 | 0.75 | >99 (99) |
| 16 | 40 | 41 | 0.5 | >99 (94) |
| 17[d] | 42 | 43 | 0.75 | >99 (99) |

[a] Reaction conditions: substrate (0.25 mmol); cis-2 (1 mol %), toluene (0.1M), 80° C.
[b] Average of 2 runs; conversions were determined by NMR; isolated yields are in brackets.
[c] 5 mol % of catalyst were used.
[d] 0.05M concentration was used.
[e] 2 mol % of catalyst were used.

Enyne ring closing metathesis is a powerful tool to synthesize dienes that can undergo further Diels-Alder reaction and thus furnish bicyclic compounds readily. Easy substrates 10 and 44 were fully converted after 30 minutes, albeit 11 was only isolated in 75% yield (Table 5 below, entries 1 & 2). A longer reaction time was necessary to convert hindered compound 46 (entry 3). Once again, a relatively low isolated yield of 71% (compared to 99% conversion) was obtained; such behaviour could result from parallel polymerization reactions that can easily occur at elevated temperature. While substrate 48 remained unchanged after 24 h of reaction, the more hindered enyne 50 was efficiently cyclized in 3 h (entries 4 & 5). Addition of ethylene is known to be necessary to allow reaction in the case of terminal alkynes such as 48. In conclusion, catalyst cis-2 allowed the formation of dienes from enynes in a short reaction time and acceptable yields.

TABLE 5

Enyne ring closing metathesis behaviour of cis-2[a]

| Entry | Substrate | Product | t [h] | conv. [%][b] |
|---|---|---|---|---|
| 1 | 10 | 11 | 0.5 | >99 (75) |
| 2 | 44 | 45 | 0.5 | >99 (99) |
| 3[c] | 46 | 47 | 19 | >99 (71) |
| 4 | 48 | 49 | 24 | 0 |
| 5 | 60 | 51 | 3 | >99 (81) |

[a]Reaction conditions: substrate (0.25 mmol), cis-2 (1 mol %), toluene (0.1M), 80° C.
[b]Average of 2 runs; conversions were determined by NMR; isolated yields are in brackets.
[c]5 mol % of catalyst were used.

The ability of catalyst cis-2 to promote intermolecular cross metathesis has also been investigated (Table 6 below). CM reactions are more difficult than their RCM counterparts as side-formation of self-metathesis products may happen. Several substrates were put in presence of 2 mol % of cis-2, together with 2 equivalents of alkene partners in toluene at 80° C. Silylated compound 12 was efficiently coupled with various olefins (entries 1-4). Indeed, the use of methyl acrylate, acrofein and diallylic acetate as alkene partners allowed the isolation of the desired products, respectively 13, 52 and 54, in good yields compared to previously reported results, thus proving that cis-2 has a good tolerance toward functional groups (entries 1, 2 and 4). However, allyltosylamine was found incompatible with our catalytic system as no conversion to 53 was observed (entry 3). Ester-containing substrates 55 and 57 bearing different chain lengths were also coupled with methylacrylate in good yields (entries 5 & 6). Both products were isolated as E isomers, the Z ones not being detected by $^1$H NMR. Reaction of eugenol 59 (essential oil of clove) with acrolein was found efficient and did not need protection of its phenolic moiety (entry 7). Finally, p-chlorostyrene 61 reacted well with methyl acrylate and gave 62 in 81% yield with an E/Z ratio of 20:1. No formation of self-metathesis compounds was observed during the testing of these substrates.

TABLE 6

Cross metathesis behaviour of cis-2[a]

| Entry | Substrate | Alkene partner | Product | t [h] | Yield [%] (E/Z)[b] |
|---|---|---|---|---|---|
| 1 | 12 (TBDMSO-) | methyl acrylate | 13 | 2 | 81 (>20:1) |

TABLE 6-continued

Cross metathesis behaviour of cis-2[a]

| Entry | Substrate | Alkene partner | Product | t [h] | Yield [%] (E/Z)[b] |
|---|---|---|---|---|---|
| 2 | | acrolein | TBDMSO-(CH2)4-CH=CH-CHO (52) | 2 | 57 (>20:1) |
| 3 | | allyl-NHTs | TBDMSO-(CH2)4-CH=CH-CH2-NHTs (53) | 3.5 | 0 |
| 4[c] | | cis-1,4-diacetoxy-2-butene | TBDMSO-(CH2)4-CH=CH-CH2-OAc (54) | 3.5 | 59 (6:1) |
| 5 | PhC(O)O-(CH2)3-CH=CH2 (55) | methyl acrylate | PhC(O)O-(CH2)3-CH=CH-CO2Me (56) | 2.5 | 85 (>20:1) |
| 6 | PhC(O)O-(CH2)2-CH=CH2 (57) | methyl acrylate | PhC(O)O-(CH2)2-CH=CH-CO2Me (58) | 2.5 | 75 (>20:1) |
| 7 | 4-allyl-2-methoxyphenol (59) | acrolein | coniferaldehyde (60) | 5 | 62 (6:1) |
| 8 | 4-chlorostyrene (61) | methyl acrylate | methyl 4-chlorocinnamate (62) | 3 | 81 (>20:1) |

[a]Reaction conditions: substrate (0.25 mmol), alkene partner (0.5 mmol), cis-2 (2 mol %), toluene (0.1M), 80° C.
[b]Average of 2 runs; isolated yields; E/Z ratios were determined by $^1$H NMR.
[c]Only 1 equiv of alkene partner was used.

Preparation of Complexes of Formulas VIII and X

Formula VIII Example

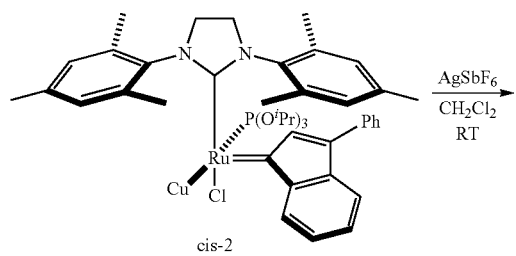

cis-2

-continued

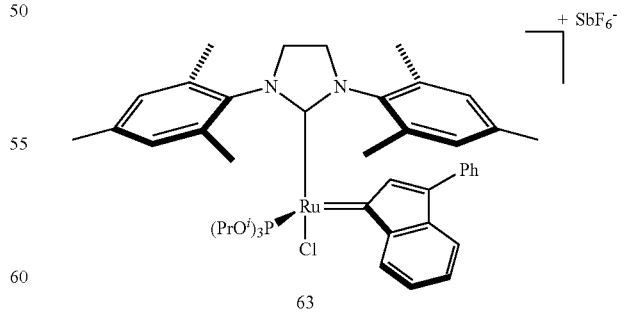

63

The complex cis-2 was reacted at room temperature with one equivalent of silver hexafluoroantimonate, yielding the pure complex 63, after simple removal of salts by filtration on celite.

$^{13}$C{$^1$H} NMR spectrum of 63 displayed a coupling constant between the carbene carbon atom and the phosphite ligand $^2J_{C-P}$ of 15.1 Hz, consistent with a cis-configuration between the NHC and the phosphite ligands. This value is very similar to the one found for cis-2 (13.4 Hz) and very far from the one found for trans-2 (127.8 Hz). Similarly, the $^2J_{C-P}$ between the indenylidene carbon atom C$^1$ and the phosphorus atom of 63 (23.2 Hz) was also found very similar with the 24.7 Hz obtained with cis-2 (trans-2 31.0 Hz).

The structure of 63 was confirmed by X-ray crystallography.

Complex 63 may be converted into an acetonitrile containing species 63a as below:

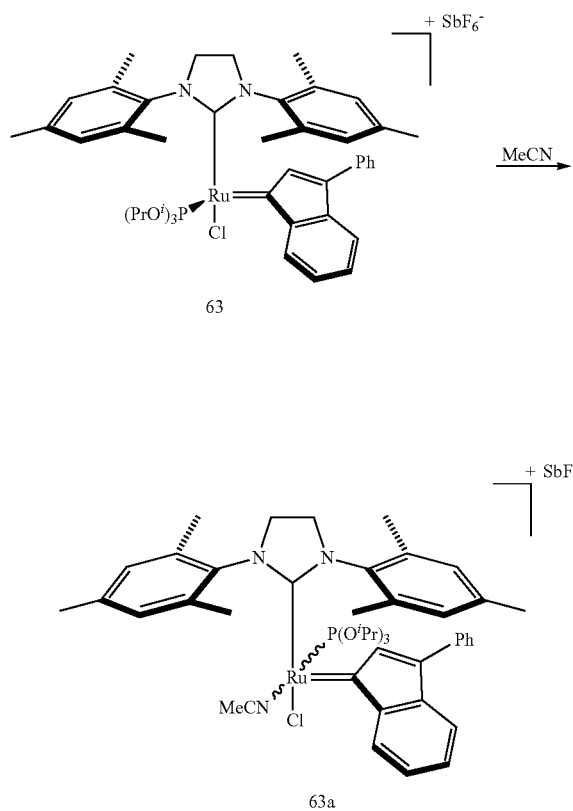

In a glove box, 63 (77.0 mg, 0.071 mmol) was dissolved in 1 mL of acetonitrile and the mixture was stirred for fifteen minutes. Solvent was removed in vacuo. The black solid was washed with hexane yielding 63a (99%).

$^1$H NMR (CD$_2$Cl$_2$, 400 MHz): δ (ppm)=1.13 (d, $^3J_{HH}$=5.6 Hz, 9H, CH—CH$_3$), 1.17 (d, $^3H_{HH}$=5.6 Hz, 9H, CH—CH$_3$), 2.02 (s, 6H, mesityl CH$_3$), 2.06 (s, 3H, CH$_3$), 2.16 (s, 6H, mesityl CH$_3$), 2.34 (s, 6H, mesityl CH$_3$), 4.01 (s, 4H, carbene CH$_2$), 4.31 (s br, 3H, CH—CH$_3$), 6.32 (s, 1H, indenylidene H), 6.74 (s, 2H, mesityl CH), 6.87 (s, 2H, mesityl CH), 7.32 (d, $^3J_{HH}$=8.0 Hz, 1H, indenylidene H), 7.41-7.50 (m, 4H, indenylidene), 7.59 (t br, $^3J_{HH}$=7.3 Hz, 1H, indenylidene H), 7.63 (d br, $^3J_{HH}$=7.3 Hz, 2H, indenylidene H), 7.83 (s, 1H, indenylidene H).

$^{31}$P{$^1$H} NMR (CD$_2$Cl$_2$, 162 MHz) δ (ppm)=115.5

The catalytic potential of 63 was first assessed for the RCM (ring closing metathesis) of the challenging tosylamine derivative 30 (Table 7) at a low catalyst loading (0.1 mol % Ru).

At 80° C., all solvents gave no or very poor conversions (Table 7, entries 1-3). Reactions carried out in xylene or mesitylene at temperatures above 110° C. (120-140° C.) gave product 31 with good conversions (76-79%) (Table 7, entries 4, 5, 9, 10). Increasing the temperature to 160° C. lead to a lower conversion to product (Table 7, entry 11). When neat conditions were used, conversion fell to 60% (Table 7 below, entry 7). Dimethyl sulfoxide or 1,2-dichlorobenzene were also found to be highly prejudicial to the reaction with a dramatic decrease of the conversion rate (Table 7, entries 6, 8).

TABLE 7

Optimization of reaction conditions.

| Entry | Solvent | T[° C.] | Conv. [%][b] |
|---|---|---|---|
| 1 | toluene | 80 | 7 |
| 2 | acetonitrile | 80 | 0 |
| 3 | iso-propanol | 80 | 1 |
| 4 | xylene | 120 | 76 |
| 5 | xylene | 130 | 77 |
| 6 | dimethyl sulfoxide | 140 | 0 |
| 7 | neat | 140 | 60 |
| 8 | 1,2-dichlorobenzene | 140 | 50 |
| 9 | mesitylene | 140 | 77 |
| 10 | xylene | 140 | 79 |
| 11 | mesitylene | 160 | 69 |

[a] Reaction conditions: 30 (0.25 mmol), 63 (0.1 mol % Ru), solvent (1 mL), 3 h.
[b] Average of 2 runs; conversions determined by GC.

Under the optimized reaction conditions (entry 10 of Table 7), the kinetic profile of 63 was recorded and compared to that of its parent neutral complex cis-2 (FIG. 5). At 140° C., cis-2 exhibits a very fast initiation and a high activity for only 3 minutes. Decomposition of the cis-2 occurred rapidly and the catalyst could not achieve more than 60% of conversion. Better results were obtained in table 4 (entry 11 above) where more catalyst and a longer reaction time was employed. In contrast, a thermal treatment of 3 minutes at 140° C. was found necessary to activate 63 indicating it can be considered a latent catalyst, which then achieved 80% conversion within 10 minutes. This shows that 63 is more thermally stable than cis-2.

The catalytic potential of 63 was than investigated for a range of dienes and enynes, under these harsh reaction conditions: 140° C., 15 min (Table 8).

TABLE 8

Metathesis reactions behavior of 63.

| Entry | Substrate | product | Cat. (mol %) | Conversion (isolated yield)[b] |
|---|---|---|---|---|
| | (2-methylallyl)₂NTs | | | 30 |
| | (allyl)₂NTs | | | 6 |
| | allyl(but-3-enyl)NTs | | | 26 |
| | (2-methylallyl)(3-methylbut-3-enyl)NTs | | | 32 |
| | diallyl malonate (diethyl) | | | 14 |
| | allyl(2-methylallyl) diethyl malonate | | | 8 |
| | diethyl di(but-3-enyl)malonate | | | 18 |
| | bis(2-methylallyl) diethyl malonate | | | 16 |
| | Ph-C(≡CH)(Me)-O-CH₂CH=CH₂ | | | 10 |
| | PhC(O)(CH₂)₃CH=CH₂ | | | 64 |
| | methyl acrylate | | | 66 |
| 1 | Ts-N(allyl)₂  6 | 1-Ts-2,5-dihydropyrrole  7 | 0.1 | 99 (90) |

TABLE 8-continued

| # | Substrate | Product | Cat. (mol%) | Yield % (isolated) |
|---|---|---|---|---|
| 2 | Allyl-N(Ts)-homoallyl (26) | N-Ts-tetrahydropyridine (27) | 0.1 | 99 (97) |
| 3 | Methallyl-N(Ts)-(3-methyl-3-butenyl) (32) | N-Ts-3,4-dimethyl-tetrahydropyridine (33) | 0.1 | 91 (85) |
| 4 | Dimethallyl-N(Ts) (30) | N-Ts-3,4-dimethyl-2,5-dihydropyrrole (31) | 0.2 | 90 (89) |
| 5 | Diethyl diallylmalonate (14) | Diethyl cyclopent-3-ene-1,1-dicarboxylate (15) | 0.2 | 99 (96) |
| 6 | Diethyl allyl(methallyl)malonate (8) | Diethyl 3-methylcyclopent-3-ene-1,1-dicarboxylate (9) | 0.1 | 99 (92) |
| 7 | Diethyl bis(3-butenyl)malonate (18) | Diethyl cyclohex-3-ene-1,1-dicarboxylate (19) | 0.1 | 99 (95) |
| 8 | Diethyl bis(methallyl)malonate (16) | Diethyl 3,4-dimethylcyclopent-3-ene-1,1-dicarboxylate (17) | 2 | 51 |
| 9 | 10 | 2-methyl-2-phenyl-3-vinyl-2,5-dihydrofuran | 0.2 | 99 (79) |

TABLE 8-continued

| 10 | 64 (1 eq.) 66 (2 eq.) |  | 0.4 | 81(72) |

[a] Reaction conditions: 63 (0.1-2 mol %), substrate (0.25 mmol), xylene (1 mL), 15 min, 140° C.
[b] Average of 2 runs; conversions were determined by GC; selected isolated yields in brackets.

Formula X Example

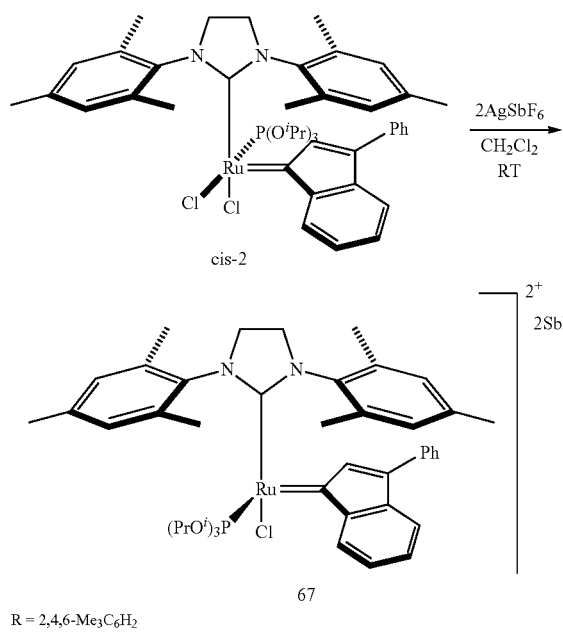

R = 2,4,6-Me$_3$C$_6$H$_2$

In a glove box, Ru complex cis-2 (0.150 g, 0.171 mmol) and silver hexafluoroantimonate (0.130 g, 0.366 mmol) and dichloromethane (5 mL) were charged in a dry flask. The reaction mixture was stirred for fifteen minutes and the solution was filtered through a plug of celite. After evaporation of solvent, pentane was added and the precipitate was collected by filtration and washed with pentane. 67 was obtained as a black greenish solid in 95% (0.1990 mg). The structure of 67 was ultimately determined by X-ray crystallography, demonstrating that a chloride had been retained and the Ru had therefore been oxidized to the III state, presumably by Ag(I) being reduced to Ag(0).

Other Examples of Complexes of Formulas I and II

A cis complex 68 comprising a phosphine and a phosphite as ligands A and Z can be made as follows:

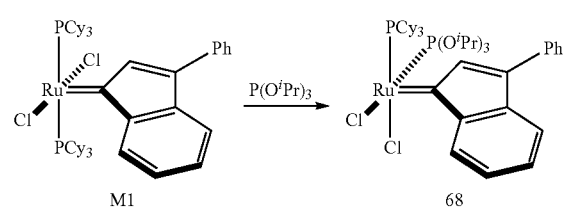

Under an inert atmosphere, triisopropylphosphite (364 µL, 1.53 mmol) was added to a solution of M1 (1.4145 g, 1.53 mmol), in dichloromethane (20 mL). The mixture was stirred for 24 h at room temperature, then the solvent was removed in vacuo. The crude was recrystallised from CH$_2$Cl$_2$/pentane. The solid was collected by filtration and washed with pentane (3×10, 2×15 mL). The product 68 was obtained as a brownish red solid (1.116 g, 85% yield).

$^1$H-NMR (400 MHz, 298K): δ (ppm)=1.10-1.35 (m, 27H), 1.40-1.55 (m, 6H), 1.60-1.85 (m, 14H), 6.79 (s, 1H, indenylidene H), 7.27 (d, J=7.1 Hz, 1H, indenylidene H), 7.43 (dd, J=6.7 Hz, J=6.3 Hz, 1H, indenylidene), 7.44 (dd, J=7.4 Hz, J=6.3 Hz, 2H, indenylidene), 7.50 (dd, J=7.4 Hz, J=7.7 Hz, 1H, indenylidene), 7.53 (dd, J=7.4 Hz, J=7.4 Hz, 1H, indenylidene), 7.76 (d, $^3$J$_{HH}$=7.3 Hz, 2H, indenylidene), 8.80 (d, J=7.3 Hz, 1H, indenylidene).

$^{31}$P-{$^1$H}-NMR (162 MHz, 298K): δ (ppm) 120.1 (d, J=37.0 Hz), 47.4 (d, J=37.0 Hz).

Following a similar procedure, with more phosphite reagent, the cis bis-phosphite complex 69 can be obtained.

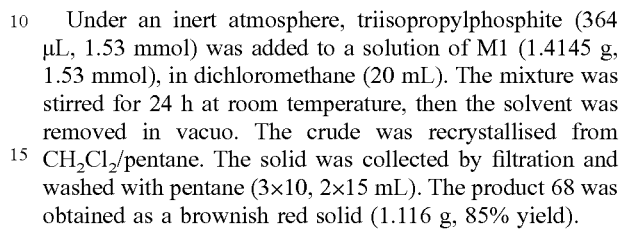

$^{31}$P-{$^1$H}-NMR (CD$_2$Cl$_2$, 162 MHz): δ (ppm)=122.9.

Further Examples of the Synthesis of Complexes and Use of the Catalysts in ROMP

Complex 1 (also known as M31) of scheme 2 was reacted with further phosphite ligands as shown below.

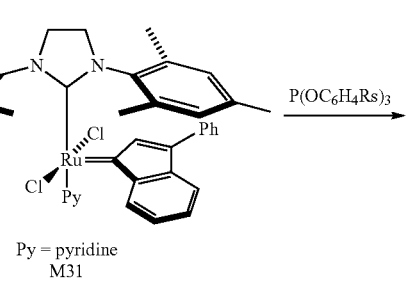

Py = pyridine
M31

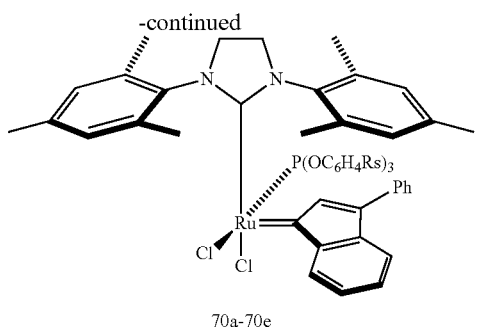

70a-70e

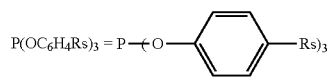

70a Rs = OMe
70b Rs = CF₃
70c Rs = Cl
70d Rs = NO₂
70e Rs = SF₅

The cis complexes 70a to 70e feature various para substituents on the phenyl rings of the phosphite ligands. These variations in the phosphite ligand can be employed to adjust catalytic activity.

The general procedure employed in manufacture was as follows:

A Schlenk flask was charged with [RuCl₂(Ind)(Py)(SIMes)] (M31) (0.5 g, 0.668 mmol), the corresponding phosphite (0.801 mmol, 1.2 eq) and dichloromethane (8 mL). The reaction was stirred at 40° C. during 15 hours, concentrated in vacuo and pentane was added. The precipitate was collected by filtration and washed with pentane.

Dichloro-{N,N'-bis[2,4,6-(trimethyl)phenyl]imidazolin-2-ylidene}Indenylidene)(p-methoxyphenylphosphite) ruthenium (70a)

Using 500 mg of M31 (0.668 mmol), the procedure afforded 479 mg (67%) of the product.
$^1$H NMR (CD$_2$Cl$_2$, 300 MHz, 233K): δ (ppm)=1.47 (s, 3H, CH$_3$), 1.90 (s, 3H, CH$_3$), 2.11 (s, 3H, CH$_3$), 2.41 (s, 3H, CH$_3$), 2.62 (s, 3H, CH$_3$), 2.75 (s, 3H, CH$_3$), 3.04 (s, 3H, O-Me), 3.65 (s, 3H, O-Me), 3.88 (s, 3H, O-Me), 3.68-4.02 (m, 4H), 5.62 (d, J=9.1 Hz, 2H), 6.05 (s, 1H), 6.10 (d, J=8.8 Hz, 2H), 6.18 (s, 2H), 6.39 (d, J=8.8 Hz, 2H), 6.57 (d, J=9.12 Hz, 2H), 6.93 (d, J=6.9 Hz, 2H), 7.08 (d, J=9.2 Hz, 3H), 7.22 (t, J=7.2 Hz, 1H), 7.33 (s, 1H), 7.26-7.39 (m, 4H), 7.42-7.49 (m, 3H), 8.61 (d, J=7.8 Hz, 1H). $^{31}$P-{$^1$H} NMR (CD$_2$Cl$_2$, 162 MHz, 298K): δ (ppm)=116.1.

Dichloro-{N,N'-bis[2,4,6-(trimethyl)phenyl]imidazolin-2-ylidene}Indenylidene)(p-trifluoromethylphenylphosphite) ruthenium (70b)

Using 500 mg of M31 (0.668 mmol), the procedure afforded 479 mg (61%) of the product.
$^1$H NMR (CD$_2$Cl$_2$, 300 MHz, 233K): δ (ppm)=1.50 (s, 3H, CH$_3$), 1.95 (s, 3H, CH$_3$), 2.09 (s, 3H, CH$_3$), 2.42 (s, 3H, CH$_3$), 2.60 (s, 3H, CH$_3$), 2.73 (s, 3H, CH$_3$), 3.72-4.05 (m, 4H), 6.00 (s, 1), 6.10 (s, 1H), 6.23 (s, 1H), 6.37 (d, J=8.25 Hz, 2H), 6.47 (d, J=8.25 Hz, 2H), 6.64 (d, J=8.25 Hz, 2H), 6.87 (d, J=7.18 Hz, 1H), 6.95 (s, 1H), 7.10 (s, 1H), 7.23 (m, 3H), 7.30 (d, J=7.45 Hz, 1H), 7.38 (m, 4H), 7.47 (m, 1H), 7.64 (d, J=8.52 Hz, 2H), 7.91 (d, J=8.52 Hz, 2H), 8.58 (d, J=7.22 Hz, 1H).
$^{31}$P-{$^1$H} NMR (CD$_2$Cl$_2$, 162 MHz, 298K): δ (ppm)=114.2.

Dichloro-{N,N'-bis[2,4,6-(trimethyl)phenyl]imidazolin-2-ylidene}Indenylidene)(p-chlorophenylphosphite) ruthenium (70c)

Using 500 mg of M31 (0.668 mmol), the procedure afforded 496 mg (66%) of the product. $^{31}$P-{$^1$H} NMR (CO$_2$Cl$_2$, 162 MHz, 298K): δ (ppm)=115.9.

Dichloro-{N,N'-bis[2,4,6-(trimethyl)phenyl]imidazolin-2-ylidene}Indenylidene)(p-nitrophenylphosphite) ruthenium (70d)

Using 500 mg of M31 (0.668 mmol), the procedure afforded 242 mg (33%) of the product.
$^{31}$P-{$^1$H} NMR (CD$_2$Cl$_2$, 162 MHz, 298K): δ (ppm)=115.3.

Dichloro-{N,N'-bis[2,4,6-(trimethyl)phenyl]imidazolin-2-ylidene}Indenylidene)(p-pentafluorosulfurphenylphosphite) ruthenium (70e)

Using 500 mg of M31 (0.668 mmol), the procedure afforded 860 mg (95%) of the product.
$^{31}$P-{$^1$H} NMR (CD$_2$Cl$_2$, 162 MHz, 298K): δ (ppm)=114.4.

As an alternative to adjusting the phosphorus containing ligand the NHC ligand may be altered to amend catalyst behaviour. For example providing bulkier ligands on the NHC can promote higher catalytic activity. For example the provision of bulkier alkyl substituents on the aromatic rings of imidazole based NHC ligands can impart improved catalyst behaviour.

The provision of isopropyl groups rather than the methyl groups of complexes such as for example complexes 70 discussed above has been shown to improve catalyst activity, in particular in ROMP polymerisation, using the polymerisation of dicyclopentadiene as an example.

Thus complex 72 prepared as shown below from the known pyridine containing complex 71 performs well in ROMP experiments. Complex 72 is prepared in a trans form as shown below, but it has been shown to behave as a latent catalyst, in particular in ROMP reactions.

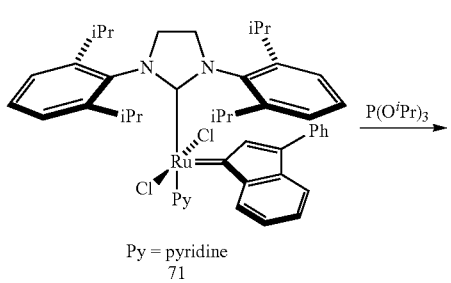

Py = pyridine
71

-continued

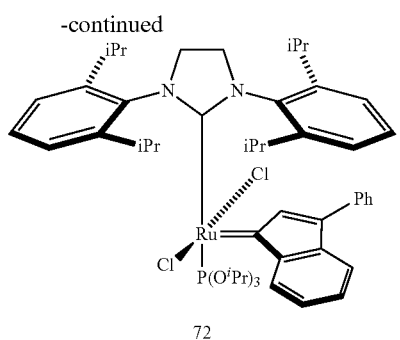

72

Inside a glovebox a solution of 71 [RuCl$_2$(SiPr)Py(Ind)] (500 mg, 0.60 mmol) in toluene (5 mL) was treated with triisopropyl phosphite (163 µL, 0.66 mmol). The reaction mixture was stirred at room temperature (for 6 h) and the solvents removed under vacuum. The resulting solid was washed affording 72 as an orange solid (460 mg, 0.48 mmol, 80%).

$^1$H NMR (CD$_2$Cl$_2$, 400 MHz): □=8.78 (d, J=7.3 Hz, 1H), 7.57 (d, J=7.3 Hz, 2H), 7.46-7.53 (m, 1H), 7.32-7.45 (m, 5H), 7.20-7.28 (m, 1H), 7.10-7.17 (m, 1H), 7.01 (d, J=7.2 Hz, 1H), 6.71-6.77 (m, 1H), 6.58-6.69 (m, 2H), 6.28 (s, 1H), 4.41-4.53 (m, 1H), 4.07-4.21 (m, 1H), 3.90-4.06 (m, 2H), 3.61-3.88 (m, 6H), 3.00 (sept, J=6.7 Hz, 1H), 1.63 (2 d, J=6.7 Hz, 6H), 1.54 (d, J=6.3 Hz, 3H), 1.26 (d, J=6.7 Hz, 3H), 1.22 (t, J=6.3 Hz, 6H), 0.95 (d, J=6.0 Hz, 9H), 0.84-0.84 (m, 1H), 0.86 (d, J=6.8 Hz, 3H), 0.74 (d, J=6.0 Hz, 9H), 0.44 ppm (d, J=6.7 Hz, 3H) $^{31}$P NMR (CD$_2$Cl$_2$, 121 MHz, CD$_2$Cl$_2$) □ 116.65 ppm. $^{13}$C NMR (CD$_2$Cl$_2$, 101 MHz) □=300.8, 217.3, 150.3, 149.9, 148.3, 147.6, 146.8, 143.5, 143.4, 141.3, 140.8, 137.7, 136.9, 136.8, 136.0, 131.6, 131.5, 130.2, 130.1, 129.5, 129.3, 128.9, 128.2, 127.1, 126.7, 125.6, 125.3, 124.7, 124.0, 117.0, 69.8, 69.2, 69.2, 55.3, 55.2, 55.1, 54.4, 54.3, 54.1, 53.6, 53.3, 30.2, 29.5, 29.3, 28.8, 27.3, 27.2, 27.1, 26.8, 25.6, 24.9, 24.4, 24.3, 24.3, 24.1, 23.8, 23.7, 23.7, 23.6, 28.0, 21.9 ppm Anal. Calcd for C$_{51}$H$_{69}$Cl$_2$N$_2$O$_3$PRu. (MW 961.05): C, 63.74; H, 5.75; N, 4.61. Found: C, 63.73; H, 7.46; N, 3.02.

ROMP Experiments

Experiments were carried out using complexes of the general form:

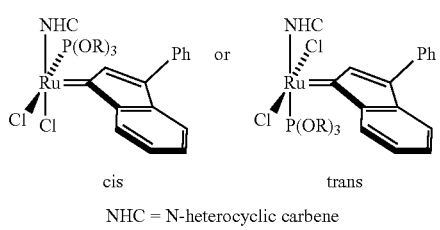

NHC = N-heterocyclic carbene where the required amount of catalyst was dissolved in dichloromethane (600 microliters) and added to dicyclopentadiene (dcpd −10 mL). The mixture was stirred, poured into the mould and heated to the required temperature to provide polydicyclopentadiene (PDCPD).

Substantial polymerisation did not occur at room temperature, showing the latency of the catalyst. However, the mixtures can form a gel at room temperature indicating some initiation of polymerisation. Heating at temperatures between 40 and 100° C. was required to provide full polymerisation. Thus a smooth controlled polymerisation could be carried out, without e.g. boiling off of the monomer due to an exotherm.

The amount of catalyst used varied between 5 to 60 ppm, based on amount of monomer.

For example, where complex 72 was employed, polymer products having a good aspect (a hard product, conforming to the mould shape) were formed. The polymers also showed good transparency and low odour. These results indicate that high conversion of monomer can be obtained. Additives such as graphite, silica or celite were added in some experiments to make a composite material.

Other complexes, including cis complexes such cis-2 described before also provided polydicyclopentadiene by the procedure described above.

REFERENCES 1. a) Nguyen, S. T.; Johnson, L. K.; Grubbs, R. H.; Ziller, J. W. *J. Am, Chem. Soc.* 1992, 114, 3974-3975. (b) Schwab, P; France, M. B.; Ziller, J. W.; Grubbs, R. H. *Angew. Chem.* 1995, 107, 2179-2181; *Angew. Chem., Int. Ed. Engl.* 1995, 34, 2039-2041.
2. Scholl, M.; Ding, S.; Lee, C. W.; Grubbs, R. H. *Org. Lett.* 1999, 1, 953-956.
3. (a) Kingsbury, J. S.; Harrity, J. P. A.; Bonitatebus, P. J.; Hoveyda, A. H. *J. Am. Chem. Soc.* 1999, 121, 791-799. (b) Garber, S. B.; Kingsbury, J. S.; Gray, B. L.; Hoveyda, A. H. *J. Am. Chem. Soc.* 2000, 122, 8168-8179.
4. (a) Grela, K.; Harutyunyan, S.; Michrowska, A. *Angew. Chem.* 2002, 114, 4210-4212; *Angew. Chem., Int. Ed.* 2002, 41, 4038-4040. (b) Wakamatsu, H.; Blechert, S. *Angew. Chem.* 2002, 114, 2509-2511; *Angew. Chem., Int. Ed.* 2002, 41, 2403-2405. (c) Zaja, M.; Connon, J.; Dunne, A. M.; Rivard, M.; Buschmann, N.; Jiricek, J.; Blechert, S. *Tetrahedron* 2003, 59, 6545-6558. (d) Michrowska, A.; Bujok, R.; Harutyunyan, S.; Sashuk, V.; Dolgonos, G.; Grela, K. *J. Am. Chem. Soc.* 2004, 126, 9318-9324.
5. For a review on ruthenium indenylidene complexes, see: Dragutan, V.; Dragutan, I.; Verpoort, F. *Platinum Met. Rev.* 2005, 49, 33-40. See also for increased stability of such complexes: Clavier, H.; Petersen, J. L.; Nolan, S. P. *J. Organomet. Chem.* 2006, 691, 5444-5477, and references therein.
6. (a) Jafarpour, L.; Schanz, H.-J.; Stevens, E. D.; Nolan, S. P. *Organometallics* 1999, 18, 5416-5419. (b) Clavier, H.; Nolan, S. P. *Chem. Eur. J.* 2007, 13, 8029-8036. (c) Boeda, F.; Bantreil, X.; Clavier, H.; Nolan, S. P. *Adv. Synth. Catel.* 2008, 350, 2959-2966. (d) Clavier, H.; Urbina-Blanco, C. A.; Nolan, S. P. *Organometallics* 2009, 28, 2848-2854.
7. a) A. Fürstner, M. Picquet, C. Bruneau, P. H. Dixneuf, *Chem. Commun.* 1998, 2249-2250; b) M. Picquet, C. Bruneau, P. H. Dixneuf, *Chem, Commun.* 1998, 1315-1316; c) A. Fürstner, M. Liebl, C. W. Lehmann, M. Picquet, R. Kunz, C. Bruneau, D. Touchard, P. H. Dixneuf, *Chem. Eur. J.* 2000, 6, 1847-1857.
8. a) S. M. Hansen, M. A. O. Volland, F. Rominger, F. Eisenträger, P. Hofmann, *Angew. Chem., Int. Ed.* 1999, 38, 1273-1276; b) P. Hofmann, M. A. O. Volland, S. M. Hansen, F. Eisenträger, J. H. Gross, K. Stengel, *J. Organomet. Chem.* 2000, 606, 88-92; c) M. A. O. Volland, S. M. Hansen, F. Rominger, P. Hofmann, *Organomet.* 2004, 23, 800-816.

9. a) Y. Miyaki, T. Onishi, H. Kurosawa, *Inorg. Chim. Acta* 2000, 369-377; b) Y. Miyaki, T. Onishi, S. Ogoshi, H. Kurosawa, *J. Organomet. Chem.* 2000, 616, 135-139.
10. D. Wang, K. Wurst, W. Knolle, U. Decker, L. Prager, S, Naumov, M. R. Buchmeiser, *Angew. Chem., Int. Ed.* 2008, 47, 3267-3270.
11. P. E. Romero, W. E. Piers, *J. Am. Chem. Soc.,* 2005, 127, 5032-5033; P. E. Romero, W. E. Piers, R. McDonald, *Angew. Chem. Int. Ed.,* 2004, 43, 6161-6165.
12. C. Slugovc, B. Perner, F. Stelzer, K Mereiter, *Organometallics,* 2004, 23, 3622-3626.
13. a) T. Ung, A. Heijl, R. H. Grubbs, Y. Schrodi, *Organometallics,* 2004, 23, 5399-5401; b) M. Barbasiewicz, A. Szadkowska, R. Bujok, K. Grela, *Organometallics,* 2006, 25, 3599-3604; c) X. Gstrein, D. Burtscher, A. Szadkowska, M. Barbasiewicz, F. Steltzer, K. Grela, C. Slugovc, *J. Polym. Sci., Part A: Polym. Chem.,* 2007, 45, 3494-3500; d) A. Ben-Asuly, E. Tzur, C. E. Diesendruck, M. Sigalov, I. Goldberg, N. G. Lemcoff, *Organometallics,* 2008, 27, 811-813; e) C. E. Diesendruck, V. Vidaysky, A. Ben-Asuly, N. G. Lemcoff, *J. Polym. Sci., Part A: Polym. Chem.,* 2009, 47, 4209-4213; f) C. E. Diesendruck, E. Tzur, A. Ben-Asuly, I. Goldberg, B. F. Straub, N. G. Lemcoff, *Inorg. Chem.,* 2009, 48, 10819-10825; g) A. Ben-Asuly, A. Aharoni, C. E. Diesendruck, Y. Vidaysky, I. Goldberg, B. F. Straub, N. G. Lemcoff, *Organometallics,* 2009, 28, 4652-4655; h) E. Tzur, A. Szadkowska, A. Ben-Asuly, A. Makal, I. Goldberg, K. Wozniak, K Grela, N. G. Lemcoff, *Chem. Eur. J.,* 2010, 16, 8726-8737.
14. M. Zirngast, E. Pump, A. Leitgeb, J. H. Albering, C. Slugovc, *Chem. Commun.,* 2011, 47, 2261-2263.

The invention claimed is:

1. A method of catalyzing a ring-opening metathesis polymerization (ROMP) reaction comprising:
   providing a reactant having at least two olefin and/or alkyne functional groups;
   providing a cis ruthenium complex according to formula I:

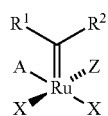

wherein for each occurrence the groups X are the same or different and are anionic ligands or are fused to form a bidentate ligand;
   the groups $R^1$ and $R^2$ are fused together to form an indenylidene ring that may be substituted or unsubstituted; and
   the group Z is selected from the group consisting of:

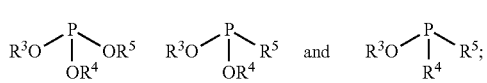

wherein the groups $R^3$, $R^4$ and $R^5$ are each independently for each occurrence selected from the group consisting of substituted or unsubstituted primary, secondary or tertiary alkyl, that may be cyclic and may be unsaturated; substituted or unsubstituted aryl or heteroaryl; and optionally two or more of the groups $R^3$, $R^4$ and $R^5$ are fused to form a ring;

the group A is selected from the group consisting of a N-heterocyclic carbine (NHC) and
   contacting the reactant with the cis ruthenium complex according to formula I for a time and at a temperature capable of causing ring-opening metathesis polymerization (ROMP).

2. The method according to claim 1 wherein the group Z is a phosphite:

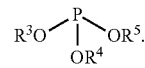

3. The method according to claim 1 wherein the anionic ligands X are independently selected from the group consisting of halogen, benzoate, and $C_1$-$C_5$ carboxylates.

4. The method according to claim 1 wherein the group A is an N-heterocyclic carbene selected from the group consisting of:

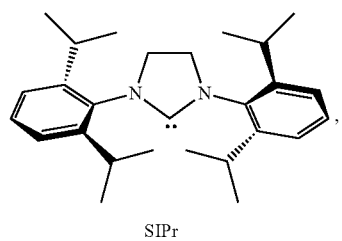

SIPr

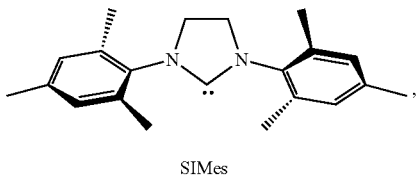

SIMes

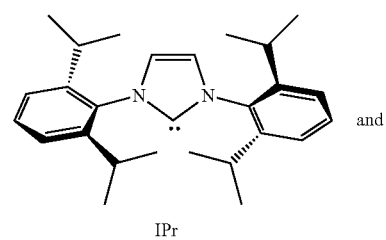

IPr and

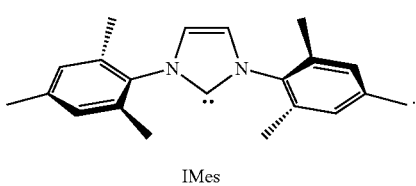

IMes

5. The method according to claim 1 wherein the ruthenium complex is:

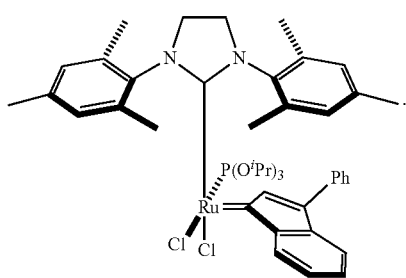

6. The method according to claim 1 wherein the ruthenium complex is according to formula XI:

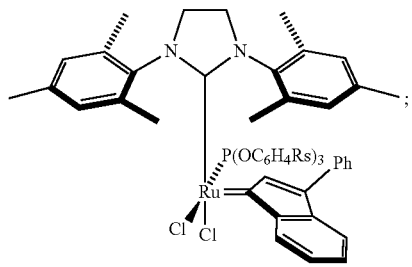

wherein the substituent Rs is selected from the group consisting of: OMe, CF₃, Cl, NO₂ and SF₅.

7. A ruthenium complex of the formula:

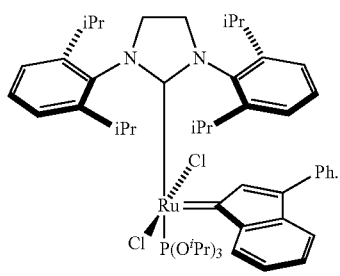

8. A ruthenium complex of the formula XI:

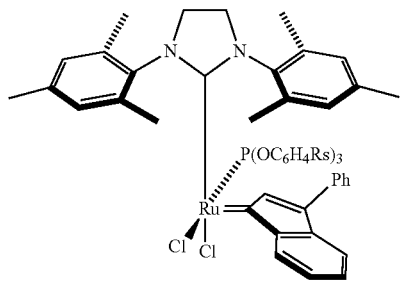

wherein the substituent Rs is selected from the group consisting of: OMe, CF₃, Cl, NO₂ and SF₅.

9. A ruthenium complex of the formula:

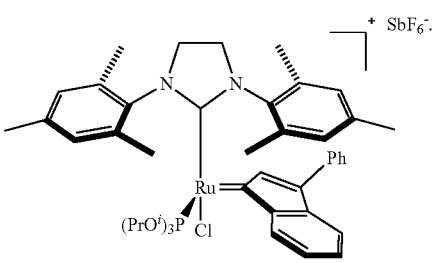

10. A ruthenium complex of the formula:

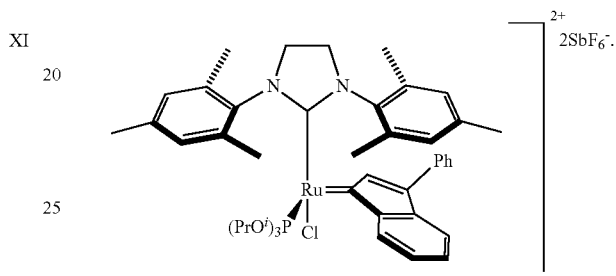

11. The method according to claim 1 wherein the anionic ligands X are independently selected from the group consisting pivalate, trifluoroacetate, $C_1$-$C_5$ alkoxy, phenoxy, $C_1$-$C_5$ alkyl thio, tosylate, mesylate, brosylate, trifluoromethane sulfonate, phenylacetate, and pseudo-halogen.

12. A method of catalyzing a metathesis reaction comprising:
introducing at least one olefin and/or alkyne functional group;
providing a cis ruthenium complex according to formula I:

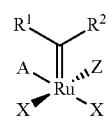

wherein for each occurrence the groups X are the same or different and are anionic ligands or are fused to form a bidentate ligand;
the groups $R^1$ and $R^2$ are fused together to form a substituted or unsubstituted indenylidene moiety that may be fused to a further ring; and
the group Z is selected from the group consisting of:

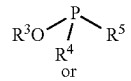
or
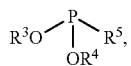

wherein the groups $R^3$, $R^4$ and $R^5$ are each independently for each occurrence selected from the group consisting of substituted or unsubstituted primary, secondary or tertiary alkyl, that may be cyclic and may be unsaturated; substituted or unsubstituted aryl or heteroaryl; and optionally, two or more of the groups $R^3$, $R^4$ and $R^5$ are fused to form a ring;

the group A is a N-heterocyclic carbene; and contacting the reactant with the cis ruthenium complex according to formula I, for a time and at a temperature capable of causing metathesis polymerization.

13. A method of catalyzing a ring-opening metathesis polymerization (ROMP) reaction comprising:

providing a reactant having at least two olefin and/or alkyne functional groups;

providing a ruthenium complex according to the formula:

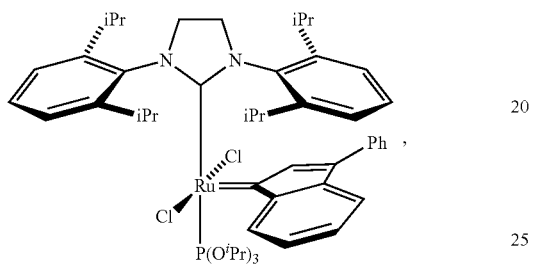

and contacting the reactant with the ruthenium complex for a time and at a temperature capable of causing ring-opening metathesis polymerization (ROMP).

* * * * *